United States Patent
Hideshima et al.

(10) Patent No.: US 10,302,644 B2
(45) Date of Patent: May 28, 2019

(54) COMPOSITIONS AND METHODS FOR TREATING MULTIPLE MYELOMA

(71) Applicant: Dana-Farber Cancer Institute, Inc., Boston, MA (US)

(72) Inventors: Teru Hideshima, Brookline, MA (US); Kenneth C. Anderson, Wellesley, MA (US); Francesca Cottini, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/524,186

(22) PCT Filed: Oct. 20, 2015

(86) PCT No.: PCT/US2015/056347
§ 371 (c)(1),
(2) Date: May 3, 2017

(87) PCT Pub. No.: WO2016/073184
PCT Pub. Date: May 12, 2016

(65) Prior Publication Data
US 2017/0356917 A1   Dec. 14, 2017

Related U.S. Application Data

(60) Provisional application No. 62/187,485, filed on Jul. 1, 2015, provisional application No. 62/074,935, filed on Nov. 4, 2014.

(51) Int. Cl.
*C12N 15/113* (2010.01)
*C12N 15/11* (2006.01)
*G01N 33/574* (2006.01)
*C12Q 1/48* (2006.01)
*G01N 33/573* (2006.01)

(52) U.S. Cl.
CPC ....... *G01N 33/57426* (2013.01); *C12Q 1/485* (2013.01); *G01N 33/573* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,399,363 A | 3/1995 | Liversidge et al. | |
| 5,415,994 A | 5/1995 | Imrich et al. | |
| 5,466,458 A | 11/1995 | Martin et al. | |
| 5,466,468 A | 11/1995 | Schneider et al. | |
| 5,543,158 A | 8/1996 | Gref et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,580,579 A | 12/1996 | Ruddy et al. | |
| 5,625,126 A | 4/1997 | Lonberg et al. | |
| 5,629,001 A | 5/1997 | Michael et al. | |
| 5,633,425 A | 5/1997 | Lonberg et al. | |
| 5,641,515 A | 6/1997 | Ramtoola | |
| 5,661,016 A | 8/1997 | Lonberg et al. | |
| 5,725,871 A | 3/1998 | Illum | |
| 5,756,353 A | 5/1998 | Debs | |
| 5,780,045 A | 7/1998 | McQuinn | |
| 5,792,451 A | 8/1998 | Sarubbi et al. | |
| 5,804,212 A | 9/1998 | Illum | |
| 5,928,639 A | 7/1999 | Slavin | |
| 6,143,292 A | 11/2000 | Slavin | |
| 6,613,308 B2 | 9/2003 | Bartus et al. | |
| 6,753,514 B2 | 6/2004 | Harashima | |
| 7,691,997 B2* | 4/2010 | Khvorova | A61K 31/713 536/24.5 |
| 7,820,809 B2* | 10/2010 | Khvorova | A61K 31/713 435/6.1 |
| 7,834,170 B2* | 11/2010 | Khvorova | A61K 31/713 536/24.1 |
| 8,090,542 B2* | 1/2012 | Khvorova | A61K 31/713 435/6.1 |
| 8,632,772 B2 | 1/2014 | Anderson et al. | |
| 8,673,593 B2 | 3/2014 | Chilcote et al. | |
| 2009/0312194 A1* | 12/2009 | Tyner | C12Q 1/485 506/10 |

FOREIGN PATENT DOCUMENTS

| | | | |
|---|---|---|---|
| WO | 2006/081251 A2 | 8/2006 | |
| WO | 2007/132156 A2 | 11/2007 | |
| WO | WO 2011/160042 | * 12/2011 | |

(Continued)

OTHER PUBLICATIONS

Morgan et al (Critical Reviews in Oncology/Hematology, 2013, S14-S22).*
Kassambara et al (Haematologica, 2010 Epub ahead of print).*
Abe et al. (2001) "Cloning and Characterization of a p53-related Protein Kinase Expressed in Interleukin-2-activated Cytotoxic T-cells, Epithelial Tumor Cell Lines, and the Testes," The Journal of Biological Chemistry. 276:44003-44011.
Badros et al. (2002) "Improved outcome of allogeneic transplantation in high-risk multiple myeloma patients after nonmyeloablative conditioning," J Clin Oncol. 20(5):1295-1303.
Cho et al. (1993) "An unnatural biopolymer," Science. 261(5126):1303-5.
DeWitt et al. (1993) "'Diversomers': An approach to nonpeptide, nonoligomeric chemical diversity," Proc Natl. Acad. Sci U S A. 90:6909-6913.

(Continued)

*Primary Examiner* — Laura B Goddard
(74) *Attorney, Agent, or Firm* — Lathrop Gage L.L.P.

(57) ABSTRACT

The invention provides, inter alia, methods of prognosing the survival of a multiple myeloma patient based levels of TP53RK in multiple myeloma cells of the patient. Also provided are methods of screening for therapeutic agents for treating multiple myeloma based on their ability to decrease TP53RK levels or activity in a patient with multiple myeloma.

6 Claims, 22 Drawing Sheets

Specification includes a Sequence Listing.

(56) References Cited

FOREIGN PATENT DOCUMENTS

WO    2013/089278 A1    6/2013

OTHER PUBLICATIONS

Dude et al. (1975) "A clinical staging system for multiple myeloma. Correlation of measured myeloma cell mass with presenting clinical features, response to treatment, and survival," Cancer. 36(3):842-54.
Erb et al. (1994) "Recursive deconvolution of combinatorial chemical libraries," Proc Natl Acad Sci U S A. 91 (24):11422-11426.
Fishwild et al. (1996) "High-avidity human IgG$_K$ monoclonal antibodies from a novel strain of minilocus transgenic mice," Nature Biotechnology. 14:845-851.
Gallop et al. (1994) "Applications of combinatorial technologies to drug discovery. 1. Background and peptide combinatorial libraries," J Med Chem. 37(9):1233-51.
Hoogenboom et al. (1992) "By-passing immunisation: Human antibodies from synthetic repertoires of germline VH gene segments rearranged in vitro," J Mol Biol. 227(2):381-8.
Hwang et al. (1998) "Gastric retentive drug delivery systems," Critical Review in Therapeutic Drug Carrier Systems. 15 (3):243-284.
Igarashi et al. (2004) "Enhanced cytotoxicity of allogeneic NK cells with killer immunoglobulin-like receptor ligand incompatibility against melanoma and renal cell carcinoma cells," Blood. 104(1):170-7.
International Preliminary Report on Patentability from PCT/US2015/056347 dated May 9, 2017.
International Search Report with Written Opinion from PCT/US2015/056347 dated Apr. 14, 2016.
Jones et al. (1986) "Replacing the complementarity-determining regions in a human antibody with those from a mouse," Nature. 321(6069):522-5.
Lonberg et al. (1994) "Antigen-specific human antibodies from mice comprising four distinct genetic modifications," Nature. 368(6474):856-9.
Maloney et al. (2003) "Allografting with nonmyeloablative conditioning following cytoreductive autografts for the treatment of patients with multiple myeloma," Blood. 102(9):3447-54.
Marks et al. (1991) "By-passing immunization: Human antibodies from V-gene libraries displayed on phage," J Mol Biol. 222(3):581-597.
Marks et al. (1992) "By-passing immunization: building high affinity human antibodies by chain shuffling," Bio/Technology. 10(7):779-83.
Mathiowitz et al. (1997) "Biologically erodable microspheres as potential oral drug delivery systems," Nature. 386: 410-414.
Morrison (1994) "Success in specification," Nature. 368:812-813.
Neuberger (1996) "Generating high-avidity human Mabs in mice," Nature Biotechnology. 14:826.
Richardson et al. (2002) "Immunomodulatory drug CC-5013 overcomes drug resistance and is well tolerated in patients with relapsed multiple myeloma," Blood. 100(9):3063-7.
Riechmann et al. (1988) "Reshaping human antibodies for therapy," Nature. 332:323-327.
Saha et al. (2012) "Targeting p53 via JNK pathway: a novel role of RITA for apoptotic signaling in multiple myeloma," PLoS One. 7(1):e30215.
Takenaga et al. (1998) "Microparticle resins as a potentil nasal drug delivery system for insulin," J Control Release. 52 (1-2):81-7.
Teoh et al. (2014) "p53 Abnormalities and potential therapeutics targeting in multiple myeloma," Biomed Research International. 2014(717919):1-9.
Tricot et al. (1996) "Graft-versus-myeloma effect: proof of principle," Blood. 87(3): 1196-8.
Verhoeyen et al. (1988) "Reshaping human antibodies: grafting an antilysozyme activity," Science. 239(4847):1534-6.
Zuckermann et al. (1994) "Discovery of Nanomolar Ligands for 7-Transmembrane G-Protein-Coupled Receptors from a Diverse N-(Substituted)glycine Peptoid Library," J. Med. Chem. 37(17):2678-2685.
Boerner et al. (1991) "Production of antigen-specific human monoclonal antibodies from in vitro-primed human splenocytes," J immunol. (147(1):86-95.
Carell et al. (1994) "A Novel Procedure for the Synthesis of Libraries Containing Small Organic Molecules," Agnew Chem Int Ed Engl. 33:2059-61.
Carell et al. (1994) "A Solution-Phase Screening Procedure for the Isolation of Active Compounds from a Library of Molecules," Agnew Chem Int Ed Engl. 33:2061-64.

\* cited by examiner

A

B

Pomalidomide-immobilized beads adapted from
PCT/US2006/002503 WO2006/081251 A2

1: MM.1S
2: H929
3: OPM1
4: OPM2
5: RPMI
6: U266
7: Dox40

A
IKZF3

COMPOSITIONS AND METHODS FOR TREATING MULTIPLE MYELOMA

CROSS REFERENCE TO RELATED APPLICATIONS

This application is a national phase entry under 35 U.S.C. § 371 of PCT/US2015/056347 filed on Oct. 20, 2015, which claims priority to U.S. Provisional Application No. 62/074,935 filed on Nov. 4, 2014 and U.S. Provisional Application No. 62/187,485 filed on Jul. 1, 2015. The contents of each of the aforementioned patent applications are hereby incorporated by reference in their entirety.

STATEMENT REGARDING FEDERALLY SPONSORED RESEARCH OR DEVELOPMENT

This invention was made with government support under grant numbers P01 CA078378, P50 CA100707, and R01 CA050947 awarded by The National Institutes of Health. The government has certain rights in the invention.

BACKGROUND

TP53-regulating kinase (TP53RK), also known as PRPK, is a serine/threonine protein kinase that phosphorylates p53 at Ser15. TP53RK is part of the KEOPS/EKC complex, which participates in transcription control and regulation of telomere length.

SUMMARY

The invention is based in part on the discovery that high levels of TP53RK are associated with shortened survival time in patients recently diagnosed with multiple myeloma.

In one aspect, the invention provides a method for screening for a candidate agent for treating multiple myeloma. The method includes providing a cell or cells expressing TP53RK, contacting the cell with a candidate therapeutic agent, and determining whether activity or expression levels of TP53RK decrease in the presence of the putative therapeutic agent as compared to activity or expression levels of TP53RK in the cell in the absence of the putative therapeutic agent. A decrease in TP53RK activity in the presence of the putative therapeutic agent indicates the test agent is a candidate agent for treating multiple myeloma.

In some embodiments, the method further comprises determining an effect of the candidate agent on hTERT and/or p53 activity in the sample.

In some embodiments, the cell expresses TP53RK binding protein (TPRKB). In some embodiments, the cell is engineered to express elevated levels of TP53RK. In some embodiments, the cells are insect cells.

In another aspect, the invention provides a method of screening a therapeutic agent for treating multiple myeloma (MM) by contacting a MM cell population with a candidate therapeutic agent that decreases activity or expression of TP53RK and assessing the effect of the candidate therapeutic agent on proliferation or migration of the MM cell population. Inhibition of multiple myeloma cell proliferation or migration indicates the test agent is a therapeutic agent for treating multiple myeloma.

The TP53RK sequences used in the screening methods can include, e.g., TP53RK polynucleotide and polypeptide sequences known in the art. Thus, in some embodiments, TP53RK sequences include the following polypeptide and polynucleotide sequences (TP53RK polypeptide-encoding sequences extend from polynucleotide 224 to 985, NCBI Reference Sequence: NM_033550.3):

```
                                                          (SEQ ID NO: 1)
MAAARATTPADGEEPAPEAEALAAARERSSRFLSGLELVKQGAEARVFRGRFQGRAAVI

KHRFPKGYRHPALEARLGRRRTVQEARALLRCRRAGISAPVVFFVDYASNCLYMEEIEG

SVTVRDYIQSTMETEKTPQGLSNLAKTIGQVLARMHDEDLIHGDLTTSNMLLKPPLEQL

NIVLIDFGLSFISALPEDKGVDLYVLEKAFLSTHPNTETVFEAFLKSYSTSSKKARPVL

KKLDEVRLRGRKRSMVG
```

```
                                                          (SEQ ID NO: 2)
  1  ggggccacaa gagcccttcc tgcagggaac ctcaggcttc agagagccga aaagttggga
 61  ggcgtaacca cttacaggcc ggaagtgtcc ggggtggacg cattcgggta gccgaagaag
121  tcccaggatt gccgaagaag tcccaggatt tccgaagcga gccgaagcat cgcgacagtt
181  ttcagagaca gctgatcggt tggagctgtt gcgccgagca gtcatggcgg cggccagagc
241  tactacgccg gccgatggcg aggagcccgc cccggaggct gaggctctgg ccgcagcccg
301  ggagcggagc agccgcttct tgagcggcct ggagctggtg aagcagggtg ccgaggcgcg
361  cgtgttccgt ggccgcttcc agggccgcgc ggcggtgatc aagcaccgct tccccaaggg
421  ctaccggcac ccggcgctgg aggcgcggct tggcagacgg cggacggtgc aggaggcccg
481  ggcgctcctc cgctgtcgcc gcgctggaat atctgcccca gttgtctttt ttgtggacta
541  tgcttccaac tgcttatata tggaagaaat tgaaggctca gtgactgttc gagattatat
601  tcagtccact atggagactg aaaaaactcc ccagggtctc tccaacttag ccaagacaat
661  tgggcaggtt ttggctcgaa tgcacgatga agacctcatt catggtgatc tcaccacctc
721  caacatgctc ctgaaacccc ccctggaaca gctgaacatt gtgctcatag actttgggct
```

-continued

```
 781  gagtttcatt tcagcacttc cagaggataa gggagtagac ctctatgtcc tggagaaggc
 841  cttcctcagt acccatccca acactgaaac tgtgtttgaa gcctttctga agagctactc
 901  cacctcctcc aaaaaggcca ggccagtgct aaaaaaatta gatgaagtgc gcctgagagg
 961  aagaaagagg tccatggttg ggtagaagaa tgtgtatgac aaccacacac agtgaagctc
1021  tttttttcaaa gtaaatttga agaaatgcta caagtatgag atgagatcta agtaaaggtg
1081  ttaagatatt tttaagtggt atgtgatcgt gtcattatca tctgcacttc actcaagagc
1141  ttactatgtg tctaagtcat gttctaggca gaattgggta tttaaagtaa attgaggaca
1201  ggcttctccc agattgtgac atgtatatct cagatacatg ggtgtggcat tgaaccacat
1261  aatgagaaca ttattctctt tttagtcctt gtgagacaag gatgaagtct cagttgctga
1321  tactcgctga gcttactggc cctctaaccc agtgttttttt tttgttgttg ttgtgtacat
1381  gttatattta ttttgaaacc agtttaatgg gatacaacca gcattttaaa aaatgaaata
1441  gaatacagca tggaaaatat cagtgtattg ttttatgaaa ctttcacgtg tatatataga
1501  ccaaggatat gtgctgagtt ttgatgtcaa atatatttct ctttcagggt catgatcaaa
1561  aaatgaaaag tctgcttaac tccaatttct cttttaaaaa agcagactta cagctttcag
1621  gcaactgaaa ttcatgttaa catgttttta tttttattgc tttgtatttt tgtggttacc
1681  ttctaagaca agtgattgat ctaaagttcc ttttaagttt ataccgctaa acaaactgag
1741  ttgatttcta tcacaggcag taagtaggta gagcaaaaat ggtgaagtga cttgtgaaga
1801  ctgaagtttg atgaagtctg gtttaaggca caggtaaact gagtgtggat gcaaaagtac
1861  caggagctag cttttaacct tgcccagcct cagtttcttt tcttagaaga agctatgttt
1921  gggtgggaag ggaagagagg gataagaaaa tacctttctt ccttgtaaac tccaatcaac
1981  aaacatattt tgagtgcctt ttgtgttcct tggcaccctg ttgggtattg ggtacttggc
2041  accctgttgg gtattgggta caatggtgag ccagacagac acagcgcctg tccttttgta
2101  agaatattta ttttttataaa aaagtataaa gtacacgtg ggatgttttg atatacatta
2161  tgaaatgatt gctacagctg agctaattaa cacccatcac ctcacatagt tactgtcttg
2221  tttcttaata tggacatttg cagctatgaa tttccctctg cacactgttg tcatcacaca
2281  ctctcagttt tggtattttg tgttttttgtt ttcattcatc tcaaagtatt ttctaatttc
2341  ccttgtgatt tcttctttga ccccttgatt gtttagaaat ctgttaattt ccacacattt
2401  gtaaatgttc caattttttct tttgttattg ccagcttcat tccattgtgt tcagagatga
2461  tacagtcagt gcctgttctt atgaagcaaa cattctataa tagtaggacc agtaccctgt
2521  ctgtttcatt caccacagtc agcatgcccc aagtgcccag catgggggcgg atggccagga
2581  atgagtgaaa acttcccttc ctgggtagtt gtgactagta gagaggaaaa ataatataat
2641  tgcctgctta ctgcatgcca ggcattgggc tgggaatttt tatattggat ctaaaataac
2701  tcttaagtta ggcattatcc ccatttttata gatggagaaa ctggccccaa aaggtgggaa
2761  cttgtccaag acgtcacagg tagcaagagg tacttttacc tggctccaaa tctgtgttct
2821  ttccactgac aaatgagata tgggatatgg tgcatcttta cagtactata ataagtattg
2881  gcgtataaca ttatttttcaa ggaactccaa gggccacagg agctgacagg ttttttcaatt
2941  aatattccca acatgaatga gatgcctcat tcctcagttt cctcacgtgt actataaggc
3001  tagtacctgc tttgttgggg tatggttggc tcgtgtgcat taagtcaaca aatccctagt
3061  tgatagggtt tggctgtgtc cccatccaaa tctcatcttg aattgttccc gtaatcccca
3121  cgtgacatgg gagggaccca gtgggaggta atttaatcct cggggcggct acctccgtgc
```

```
3181   tgttctcgtg atagcgagtg agttctcacg agatctgatg gttttataag gggcttttcc 3241   ctcttgttcg gcacttcctg ctgccacgtg gagaagggtg tgtttgtttc cccatctgcc 3301   atgattataa gttttctgag gcatccccag ccatgctgaa ctgtgagtta ttaaactttt 3361   cctttataaa ttaaaaaaaa aaaa
```

In some embodiments, a TPRKB polypeptide sequence includes the following amino acid sequence, as well as a polynucleotide sequence encoding the polypeptide (from *Homo sapiens* TP53RK binding protein (TPRKB), mRNA NCBI Reference Sequence: NM_016058.2):

```
                                              (SEQ ID NO: 3)
MQLTHQLDLFPECRVTLLLFKDVKNAGDLRRKAMEGTIDGSLINPTVIVDPFQILVAANKAVHLYKLGKMK

TRTLSTEIIFNLSPNNNISEALKKFGISANDTSILIVYIEEGEKQINQEYLISQVEGHQVSLKNLPEIMNI

TEVKKIYKLSSQEESIGTLLLDAIICRMSTKDVL
```

```
                                              (SEQ ID NO: 4)
  1   gaagaagacg gggattggcc atcgcttccg gaagttgtga gctttgtttc ggagcgggag 61   ctcttccgag acgcactggg ggccggatgt agaatcctgc ttatctgtga aatgcagtta 121   acacatcagc tggacctatt tcccgaatgc agggtaaccc ttctgttatt taaagatgta 181   aaaaatgcgg gagacttgag aagaaaggcc atggaaggca ccatcgatgg atcactgata 241   aatcctacag tgattgttga tccatttcag atacttgtgg cagcaaacaa agcagttcac 301   ctctacaaac tgggaaaaat gaagacaaga actctatcta ctgaaattat tttcaacctt 361   tccccaaata acaatatttc agaggctttg aaaaaatttg gtatctcagc aaatgacact 421   tcaattctaa ttgtttacat tgaagaggga gaaaaacaaa taaatcaaga atacctaata 481   tctcaagtag aaggtcatca ggtttctctg aaaaatcttc ctgaaataat gaatattaca 541   gaagtcaaaa agatatataa actctcttca caagaagaaa gtattgggac attattggat 601   gctatcattt gtagaatgtc aacaaaagat gttttatgaa atgtcagaaa tattaacaaa 661   aattctcagc attaaagaaa acattgattt tcctttcctg actataaaac taattgtgca 721   ttatagaaaa gtttaaatca cagaatggta tt
```

In various embodiments, the cell is provided in vitro, in vivo, or ex vivo.

In some embodiments, the cell is a lymphocyte. In some embodiments, the cell is a B cell or a plasma cell. In some embodiments, the cell is a multiple myeloma cell.

In some embodiments, the candidate therapeutic agent is a nucleic acid, a polypeptide, a small molecule or combinations thereof.

The nucleic acid can be, e.g., an inhibitory nucleic acid. An inhibitory nucleic acid can be, e.g., a triplex forming oligonucleotide, an aptamer, a ribozyme, an antisense RNA, a short interfering RNA (siRNA), or a micro-RNA (miRNA).

In some embodiments, the candidate therapeutic polypeptide is an antibody, e.g., an anti-TP53RK antibody (such as a humanized anti-TP53RK antibody).

Also provided by the invention is a method of inhibiting proliferation or migration of a multiple myeloma cell by administering a therapeutic agent in an amount effective to inhibit proliferation or migration of the multiple myeloma cell. In various embodiments, the therapeutic agent encodes a TP53RK shRNA or siRNA.

In some embodiments, the multiple myeloma cell is provided in vivo and is present in a subject diagnosed with, or believed to have, multiple myeloma.

In some embodiments, the shRNA is aTP53RK shRNA.

In some embodiments, the shRNA is specific for the target sequence CAGTCCACTATGGAGACTGAA (SEQ ID NO:5).

In some embodiments, the therapeutic agent is a TP534K siRNA, e.g., the siRNA is one or more of the following:

```
TP53RK J-003108-09
                            (SEQ ID NO: 6)
GGUAGAAGAAUGUGUAUGA

TP53RK J-003108-10
                            (SEQ ID NO: 7)
GCUUCCAACUGCUUAUAUA,

TP53RK J-003108-11
                            (SEQ ID NO: 8)
GCUGAACAUUGUGCUCAUA,
or

TP53RK J-003108-12
                            (SEQ ID NO: 9)
GUACCCAUCCCAACACUGA.
```

In another aspect, the invention provides a kit for prognosing, diagnosing, staging or monitoring multiple myeloma in a patient. The kit includes a reagent suitable for determining levels of a TP53RK RNA or protein in a biological sample obtained from a subject.

The reagent can be, e.g., a TPRK53 antibody (and can be a monoclonal or polyclonal antibody).

The kit can additionally include reagents for performing an ELISA assay, and/or a lateral flow assay.

In some embodiments, the reagent is one or more nucleic acids that specifically bind to a TP53RK nucleic acid.

In another aspect, the invention provides a method of determining the prognosis of a human multiple myeloma patient. The method includes obtaining from the patient a test sample comprising multiple myeloma cells and measuring TP53RK activity or expression in the test sample. TP53RK activity or expression is compared in the test sample to TP53RK activity or expression in a control sample from a subject whose multiple myeloma status is known. A prognosis is assigned to the patient on the basis of the comparison. Increased TP53RK activity or expression relative to TP53RK activity or expression in a control sample of a plasma cell or cells from a subject not having multiple myeloma indicates a poor prognosis, while the same or decreased TP53RK activity or expression relative to TP53RK activity or expression of TP53RK in subject not having multiple myeloma indicates a good prognosis.

In another aspect, the invention provides method of diagnosing multiple myeloma in a human patient. The method includes obtaining from the subject a test sample comprising plasma cells, measuring TP53RK activity or expression in the test sample and comparing the TP53RK activity or expression in the test sample to TP53RK activity or expression in a control sample from a subject whose multiple myeloma status is known. A multiple myeloma diagnosis is assigned to the patient on the basis of the comparison: increased TP53RK activity or expression relative to TP53RK activity or expression in a control sample of a plasma cell or cells from a subject not having multiple myeloma indicates the subject has multiple myeloma, and the same or decreased TP53RK activity or expression relative to TP53RK activity or expression of TP53RK in subject not having multiple myeloma indicates the subject does not have multiple myeloma.

In a still further aspect, the invention provides a method for determining efficacy of a multiple myeloma treatment in a multiple myeloma patient. The method comprises providing a sample from a subject with multiple myeloma and assaying the sample to determine a level of TP53RK in the sample to obtain a TP53RK test value. The TP53RK test value is compared to a TP53RK reference value calculated for a sample whose multiple myeloma status is known. A TP53RK test value greater than a reference TP53RK value in a reference sample known not to have multiple myeloma indicates that the treatment is not efficacious, and a TP53RK test value less than a reference TP53RK value in a sample known to have multiple myeloma indicates that the treatment is efficacious.

In some embodiments, the reference sample is obtained from the same patient prior to beginning treatment of multiple myeloma in the subject or at a previous point in treatment of multiple myeloma in the subject.

In some embodiments, the reference sample is obtained from one or more reference samples obtained from subjects whose multiple myeloma status is known.

In some embodiments, the method further comprises creating a record indicating the subject is likely to respond to the treatment for a longer or shorter duration of time based on TP553RK activity or expression.

Preferably, the record is created on a tangible medium, e.g., a computer readable medium.

In a further aspect, the invention provides a method for monitoring the progression of multiple myeloma in a patient. The method includes obtaining from the patient a test sample comprising multiple myeloma cells and measuring TP53RK activity or expression in the test sample. TP53RK activity or expression is compared in the test sample to TP53RK activity or expression in a control sample from a subject whose multiple myeloma status is known. The progression of multiple myeloma in the patient on the basis of the comparison is assessed: increased TP53RK activity or expression relative to TP53RK activity or expression in a control sample of a plasma cell or cells from a subject not having multiple myeloma indicates the multiple myeloma is worsening in the patient, while the same or decreased TP53RK activity or expression relative to TP53RK activity or expression of TP53RK in subject not having multiple myeloma indicates the multiple myeloma is not worsening in the patient.

In some embodiments, the control sample comprises multiple myeloma cells removed prior to beginning treatment of multiple myeloma or at a previous point in treating multiple myeloma in the patient.

Embodiments of the various prognostic, diagnostic, efficaciousness-related, progression-related aspects disclosed herein can include, e.g., a patient undergoing, or who has previously underwent, treatment comprising chemotherapy and/or autologous peripheral blood stem cell transplantation.

The sample can be, e.g., a serum sample. In other embodiments, the sample is obtained from bone marrow cells (such as bone marrow mononuclear cells).

In some embodiments, the method includes measuring the amount of TP53RK polypeptide in the sample.

Preferably, the amount or activity of TP53RK is measured in a quantitative assay. Examples of quantitative assay include a quantitative immunoassay. A quantitative immunoassay can be, e.g., ELISA, western blotting, immunoaffinity chromatography, flow cytometry, or immunohistochemistry.

In some embodiments, the quantitative assay is HPLC, mass spectrometry, protein microarray analysis, PAGE analysis, isoelectric focusing, or two-dimensional gel electrophoresis analysis.

In other embodiments, the method includes measuring the amount of TP53RK transcripts in the sample. In one embodiment, TP53RK transcript detection includes generating a TP53RK cDNA from a TP53RK RNA.

Preferably, measuring is by quantitative transcription detection, e.g., a transcription-based amplification system (TAS).

Examples of quantitative transcription detection methods include QRT-PCR-based amplification systems, ligase chain reaction, Qβ, replicase, reverse transcriptase-coupled nucleic acid sequence-based amplification (NASBA), self-sustained sequence replication (3SR), strand displacement amplification (SDA), or reverse transcriptase-coupled rolling circle amplification (RCA).

In some embodiments, quantitative transcription detection is performed by detecting a complex between an artificially and detectably labeled TP53RK-nucleic acid sample and a synthetic microarray.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention are apparent from the following description, and from the claims.

DESCRIPTION OF DRAWINGS

Some of the figures in the application were executed in color.

FIG. 1A is a Western blot of MM.1S cells cultured with Len (2.5 µM) or Pom (2.5 µM) in the presence (40 nM) or absence of Dox for 48 h.

FIGS. 1B and 1C are a Western blot and histogram, respectively, of MM.1S and H929 cells treated with Len (1.3 µM) or Pom (3 µM) for 48 h. Nuclear proteins were subjected to (B) immunoblotting or (C) p53 DNA binding activity assay (MM.1S, □; H929 ■). Nucleolin (Nuc) served as a loading control.

FIG. 1D is a Western blot of MM.1S cells treated with Len (2.5 µM) or Pom (2.5 µM) in the presence or absence of Dox (40 nM) for 48 h.

FIG. 1E is a representation of a 3'-n-butylamine derivative of Pom synthesized and attached via linker to generate Pom-based affinity reagent.

FIGS. 1F and G are Western blot analyses of protein lysates pulled down by Pom-beads (F), Thal-beads (G), or whole cell lysate (W.L.) and subjected to Western blotting using anti-CRBN Ab (upper panel). Membranes were subsequently immunoblotted with anti-TP53RK Ab without stripping.

FIG. 1H is a Western blot analysis of recombinant C-terminal Myc-DDK tagged TP53RK and TPRKB proteins from HEK-293FT cells subjected to vitro auto-phosphorylation at varying concentrations of Pom.

FIG. 1I is a Western blot analysis of results obtained when TP53RK was knocked down in MM.1S cells.

FIG. 1J is a Western blot analysis of results obtained when MM.1S cells were treated with Thal or Pom for 48 h.

FIG. 2A is a graphical representation of a comparative GEP analysis of TP53RK between normal PCs and MM cells.

FIG. 2B is a graphical representation of the overall survival relative to TP53RK expression in patients with newly diagnosed MM (log-rank test).

FIG. 2C is a histogram of MM.1S cells infected with control (Luc) or TP53RK (#1, #2) shRNAs. Cell growth was assessed by a MTT assay.

FIG. 2D is a Western blot analysis of the results obtained when CRBN was knocked down by shRNAs in MM.1S cells.

FIG. 2E is a Western blot analysis of results obtained by siRNA knockdown of CRBN or TP53RK in H929 cells.

FIG. 2F is a histogram of cell viability for the cells shown in FIG. 2E. Viable cells were counted using Trypan-blue.

FIG. 2G is a Western blot analysis of MM.1S cells treated with Len or Pom for 48 h.

FIG. 2H is a graphical representation of H929 cells transfected with control, wild-type (wt), or TP53RK kinase dead mutant (D163A), and viable cells enumerated by Trypan blue.

FIG. 2I is a Western blot analysis of transfectants treated with Len or Pom for 48 h. Viable cells were counted using Trypan-blue.

FIG. 2J is a Western blot analysis of H929 cells transfected with scrambled (Sc) or TP53RK siRNA followed by Pom treatment for 48 h. H929 cells were transfected with Sc or CRBN siRNA followed by Len or Pom treatment for 48 h. Cell growth was assessed by MTT assay. All immunoblotting (D,E,G) of cell lysates was carried out using indicated Abs.

FIG. 2K is a graphical representation of the effect of CRBN knock-down in OPM2 and H929 cells exposed to Len or Pom.

FIG. 3A is a Western blot analysis of the results obtained when MM.1S cells (left panel) and H929 cells (right panel) were infected with lentiviral scrambled (Sc) or p53 shRNA/siRNA, respectively.

FIG. 3B is a Western blot analysis of the results obtained when H929 cells were treated with Len (1.25-5 µM) or Pom (1.25-5 µM) for 48 h.

FIG. 3C shows a Western blot analysis of the results obtained when MM.1S cells were cultured with Len (2.5 µM) or Pom (2.5 µM) in the presence (0.5 µM) or absence of Nutlin-3a for 48 h.

FIG. 3D is a Western blot analysis of the results obtained when MM.1S cells were infected with lentiviral Sc or p53 shRNA for 48 h.

FIG. 3E is a Western blot analysis of the results obtained when MM.1S cells were treated with Len for 48 h.

FIG. 3F is a Western blot analysis of the results obtained when MM.1S cells were infected with Sc or p53 shRNA.

FIG. 3G is a histogram showing the fold change in c-Myc or p53 mRNAs when extracted from transfectants and subjected to real-time qPCR.

FIG. 3H is a graph showing the delineation of c-MYC binding to promoter regions in IKZF1.

FIG. 3I is a histogram showing the relative mRNA levels from H929 cells when transfected with Sc or c-Myc siRNA. Extracted mRNA was subjected to qPCR for IKZF1/3.

FIG. 3J is a Western blot showing the results obtained when MM.1S cells were infected with Luc or c-Myc shRNA.

FIG. 3K is a graph showing the correlation of gene expression between c-Myc and IKZF1 (left panel) and TP53RK and IKZF1 (right panel). All immunoblotting (A-F and J) was carried out using whole cell lysates and indicated Abs.

FIGS. 4A-Q demonstrate the mechanism of action for TP53RK triggered anti-MM activities.

FIGS. 4A-B are a histogram (A) and Western blot (B) showing expression values for RRM1 from H929 cells transfected with Sc or TP53RK siRNA.

FIG. 4C is a Western blot showing downregulation RMM1 in H929 cells transfected with Sc or TP53RK siRNA.

FIG. 4D is a histogram showing viable cell count of H929 cells transfected with Sc or TP53RK siRNA.

FIGS. 4E-F depict a histogram (E) and Western blot (F) confirming upregulation of p18.

FIGS. 4G-H are a histogram (E) and Western blot (F) showing downregulation of RMM1 and upregulation of p18 in H929 cells were treated with Len or Pom for 48 h.

FIG. 4I shows gene expression profiling analysis (GSEA) before and after TP53RK knock down in H929 cells transfected with Sc or TP53RK siRNA.

FIG. 4J is a histogram showing the downregulation of relative mRNA expression of PSMB5, PSMB7 and PSMA3.

FIG. 4K is a histogram showing proteosome activity in H929 cells transfected with Sc or TP53RK siRNA.

FIG. 4L is a Western blot showing accumulation of poly-ubiquinated proteins in H929 cells transfected with Sc or TP53RK siRNA.

FIG. 4M shows gene expression profiling analysis (GSEA) in H929 cells treated with Pom for 48 h.

FIG. 4N is a Western blot showing the downregulation of hTERT in H929 cells were transfected with Sc or TP53RK siRNA.

FIG. 4O shows gene expression profiling analysis (GSEA) in MM.1S cells treated with Len or Pom for 48 h.

FIG. 4P is a Western blot showing the inhibition of hTERT expression in MM1S cells treated with Len and Pom.

FIG. 4Q is a histogram showing telomerase activity in MM1S cells treated with Len and Pom.

FIG. 19A is a figure showing CHIP-seq tag counts in the vicinity (+/−5 kb) of the transcription start site (TSS) of IKZ3 with data displayed as normalized (average reads per million/RMP0 c-MYC (blue) or control (red).

FIG. 19B shows whole cell immunoblot analyses of H929 cells transfected with scrambled or TP53RK siRNA.

FIG. 19C shows whole cell immunoblot analyses of H929 cells transfected with scrambled or CRBN siRNA.

FIG. 20A shows H929 cells treated with DMSO control, Len (1 μM), or Pom (1 μM) for 48 hours.

FIG. 20B shows H929 cells transfected with Sc, TP53RK, or CRBN siRNA. The cells were subjected to a chymotrypsin-like proteasome assay.

FIG. 20C shows H929 cells transfected with Sc or TP53RK, followed by BTZ (3 nM treatment) for 24 h. Cell growth was assessed by a MTT assay.

FIG. 21A shows the effect of Len (2 μM) or Pom (2 μM) using a "TeloTAGGG Telomerase PCR ELISA®" assay to assess telomerase activity.

FIG. 21B is a comparative hTERT expression analysis in matched samples of MM patients before (PRE_LEN) and after (POST_LEN) treatment with Len (GSE8546 dataset).

DESCRIPTION

Figure 1:
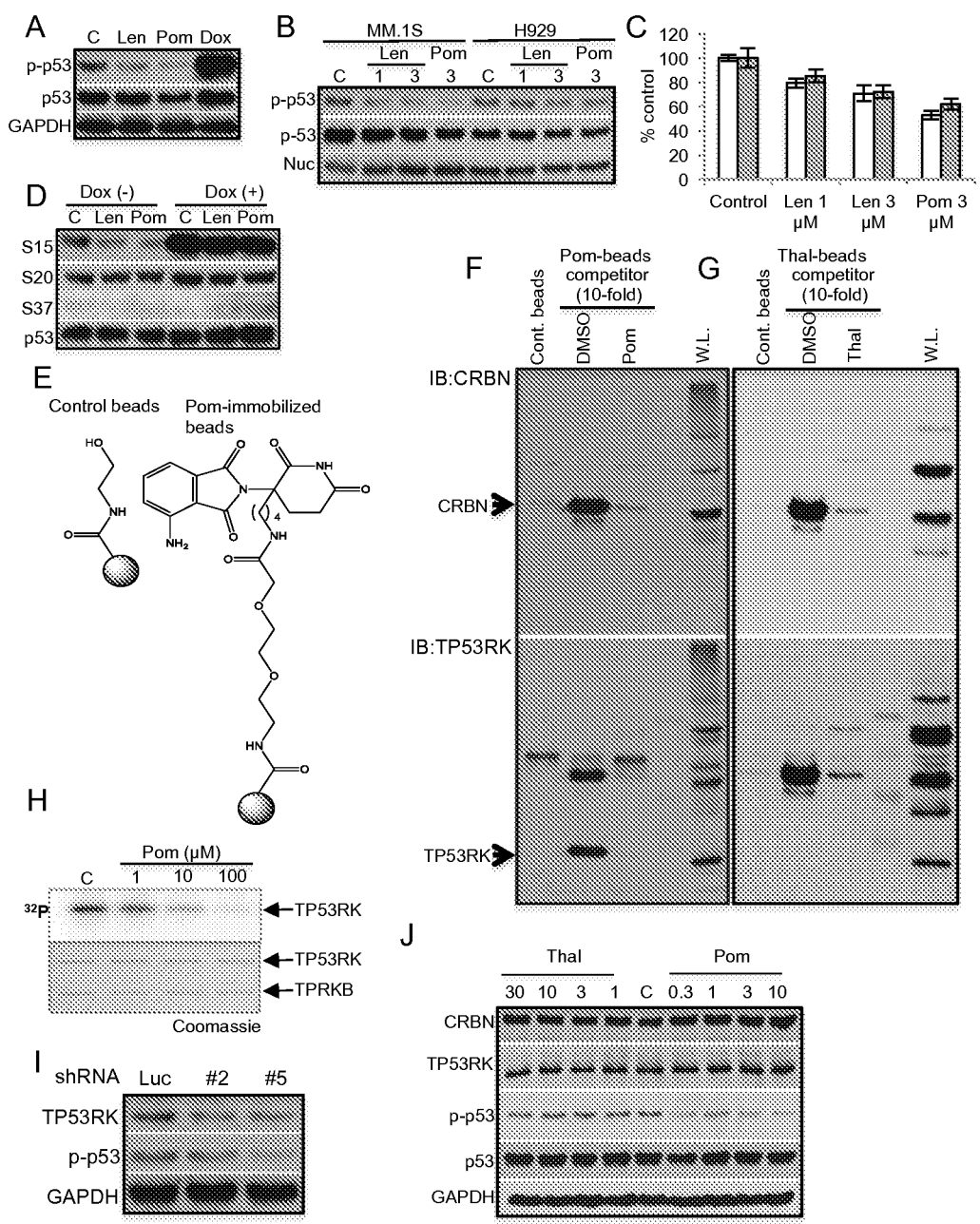
FIGS. 1A-J show that IMiDs bind to TP53RK and downregulate p (Ser15)-p53.

The invention provides methods and compositions that are based in part on the discovery that recently diagnosed multiple myeloma patients with elevated levels of TP53RK have a poor prognosis relative to multiple myeloma patients who do not have elevated levels of TP53RK.

Multiple myeloma (MM) is an incurable plasma cell disorder; however, novel biologically-based therapeutic agents including immunomodulatory drugs (IMiDs) thalidomide, lenalidomide, and pomalidomide have remarkably improved patient outcome. Recent studies have delineated molecular mechanisms whereby IMiDs trigger anti-MM activities.

We show that pomalidomide binds not only to cereblon (CRBN), but also to p53-related protein kinase (TP53RK, also known as PRPK) and blocks its activity, resulting in inhibition of its only known downstream target, p53. Indeed, knockdown of TP53RK shows significant MM cytotoxicity. We show that inhibition of p53 activity via TP53RK: (1) decreases MDM2 and downstream XIAP as well as activates E2F-dependent Bim, thereby mediating both apoptotic and autophagic MM cell death; and (2) downregulates c-Myc and its target IKZF1/3. IMiDs therefore regulate IKZF1/3 expression via CRBN and proteasomal degradation, as well as transcriptional inhibition of cMyc via TP53RK-p53 axis. Importantly, TP53RK knockdown also identifies novel interacting proteins, including ribonucleotide reductase (RRM1), p18CDKN2C, and telomerase reverse transcriptase (TERT). We confirmed that RRM1 downregulation showed significant MM cytotoxicity. The inventions described herein are based in part on novel molecular mechanisms of IMIDs-mediated anti-MM activity defined herein and identify novel potential therapeutic targets in MM.

Determining the Prognosis of a Multiple Myeloma Patient

To determine the prognosis of a patient diagnosed with multiple myeloma, a test sample is obtained that includes multiple myeloma cells or plasma cells suspected to be multiple myeloma cells. TP53RK activity or gene expression in the test sample is measured using methods known in the art and described herein. The measured TP53RK activity or expression in the test sample to is compared to TP53RK activity or expression in the test sample to TP53RK activity or expression in a control sample from a subject whose multiple myeloma status is known, and the patient is assigned a prognosis on the basis of the comparison. Increased TP53RK activity or expression relative to TP53RK activity or expression in a control sample of a plasma cell or cells from a subject not having multiple myeloma indicates a poor prognosis, and the same or decreased TP53RK activity or expression relative to TP53RK activity or expression in a subject not having multiple myeloma indicates a good prognosis.

The methods can be used when a patient is undergoing, or previously underwent, treatment such as chemotherapy and/or autologous peripheral blood stem cell transplantation.

In general, any bodily fluid can be used, provided it includes a plasma cell expressing TP53RK, or a fraction in which TP53RK activity can be detected. In various embodiments, the test sample is obtained from a serum sample. In other embodiments, the sample is obtained from culture of bone marrow cells of the patient, e.g., bone marrow mononuclear cells. Additional cell or tissue sources can also be used provided they include or are suspected of including cells expressing TP53RK activity, e.g., body fluid or secretion including but not limited to seminal plasma, blood, serum, urine, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, broncho alveolar lavage, lavage of the reproductive system and/or lavage of any other part of the body or system in the body, and stool or a tissue sample. The term may also optionally encompass samples of in vivo cell culture constituents. The sample can optionally be diluted with a suitable eluant before contacting the sample to an antibody and/or performing any other diagnostic assay.

In some embodiments, the amount of TP53RK polypeptide in the sample is measured, e.g., in a quantitative assay. By "quantitative assay" is meant the determination of the level, quantity or amounts of protein or nucleic acid sequences in the sample, on which a detection process is performed. In some embodiments, detection is with a device or machine.

In some embodiments, the quantitative assay is a quantitative immunoassay, e.g., ELISA, western blotting, immunoaffinity chromatography, flow cytometry, or immunohistochemistry.

In some embodiments, the quantitative assay is HPLC, mass spectrometry, protein microarray analysis, PAGE analysis, isoelectric focusing, or two-dimensional gel electrophoresis analysis.

If desired, prognosis is determined by determining the amount of TP53RK transcripts. Transcription detection is preferably by quantitative transcription. In some embodiments, quantitative transcription detection is performed using a transcription-based amplification system (TAS), e.g., in a method that includes generating a TP53RK cDNA from a TP53RK RNA.

In various embodiments, quantitative transcription detection is QRT-PCR-based amplification systems, ligase chain reaction, Qβ, replicase, reverse transcriptase-coupled nucleic acid sequence-based amplification (NASBA), self-sustained sequence replication (3SR), strand displacement amplification (SDA), or reverse transcriptase-coupled rolling circle amplification (RCA).

In some embodiments, quantitative transcription detection is by detecting a complex between an artificially and detectably labeled TP53RK-nucleic acid sample and a synthetic microarray.

Similarly, the methods described above for determining the prognosis of a multiple myeloma patient can be adapted to diagnosing multiple myeloma in a human patient, determining efficacy of a multiple myeloma treatment in a multiple myeloma patient, and/or determining the progression of multiple myeloma in a patient.

When determining the progression of multiple myeloma, the reference sample can obtained from the same patient prior to beginning treatment of multiple myeloma in the subject or at a previous point in treatment of multiple myeloma in the subject. Alternatively, the reference sample can be obtained from one or more reference samples obtained from subjects whose multiple myeloma status is known.

The methods preferably include creating a record indicating the subject is likely to respond to treatment for a longer or shorter duration of time based on TP553RK activity or expression. Preferably, the record is created on a tangible medium such as a computer readable medium.

The link identified by the inventors between TP53RK and multiple myeloma (MM) also provides new methods for diagnosing and otherwise assessing MM in a subject. Multiple myeloma (MM) or a multiple myeloma precursor condition (provided it is associated with elevated TP53RK activity) in a subject can be diagnosed by providing a sample from the subject and assaying the sample to determine a level of TP53RK in the sample to obtain a TP53RK test value. The test value is compared to a TP53RK reference value calculated for a sample from a patient or patients whose MM status is known. A TP53RK test value greater than a TP53RK value in a reference sample from a patient or patients known not to have MM indicates that the subject has MM. Conversely, a TP53RK test value equal to or less than a reference TP53RK value in a sample known to have MM indicates that the subject does not have multiple myeloma.

Similarly, efficaciousness of a treatment for multiple myeloma can be determined by providing a sample from a subject with MM and assaying the sample to determine a level of TP53RK in the sample to obtain a TP53RK test value. The TP53RK test value is compared to a TP53RK reference value calculated for a sample from a patient or patients whose MM status is known. A TP53RK test value greater than a reference TP53RK value in a reference sample known not to have MM indicates that the treatment is not efficacious, and a TP53RK test value less than a reference TP53RK value in a sample known to have MM indicates that the treatment is efficacious. In some embodiments, the reference sample is obtained from the same subject prior to beginning treatment of MM or at an earlier point in treatment of MM.

The progression of multiple myeloma (MM) in a subject can also be determined; a TP53RK test value greater than a reference TP53RK value in a sample known not to have MM indicates that the subject has a MM more advanced than MM in subjects from which the reference TP53RK value is calculated, while a TP53RK test value less than the reference TP53RK value indicates that the subject has a MM less advanced than MM in subjects from which the reference TP53RK value is calculated.

The threshold for determining how a test sample is scored in the assays described herein, e.g., whether a test sample is scored positive, can be altered depending on the sensitivity or specificity desired. The clinical parameters of sensitivity, specificity, negative predictive value, positive predictive value and efficiency are typically calculated using true positives, false positives, false negatives and true negatives. A "true positive" sample is a sample that is positive according to an art recognized method, which is also diagnosed as positive (high risk for early attack) according to a method of the invention. A "false positive" sample is a sample negative by an art-recognized method, which is diagnosed positive (high risk for early attack) according to a method of the invention. Similarly, a "false negative" is a sample positive for an art-recognized analysis, which is diagnosed negative according to a method of the invention. A "true negative" is a sample negative for the assessed trait by an art-recognized method, and also negative according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of the measured trait. Sensitivity is calculated as the number of true positive results divided by the sum of the true positives and false negatives. Sensitivity essentially is a measure of how well a method correctly identifies those with disease. For example, cut-off values can be selected such that the sensitivity of diagnosing an individual is at least about 60%, and can be, for example, at least about 50%, 65%, 70%, 75%, 80%, 85%, 90% or 95%.

As used herein, the term "specificity" means the probability that a method is negative in the absence of the measured trait. Specificity is calculated as the number of true negative results divided by the sum of the true negatives and false positives. Specificity essentially is a measure of how well a method excludes those who do not have the measured trait. For example, cutoff values can be selected so that when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having the measured trait actually has the disease. Positive predictive value can be calculated as the number of true positives divided by the sum of the true positives and false positives. Positive predictive value is determined by the characteristics of the diagnostic method as well as the prevalence of the disease in the population analyzed. The cut-off values can be selected such that the positive predictive value of the method in a population having a disease prevalence of 15% is at least about 5%, and can be, for example, at least about 8%, 10%, 15%, 20%, 25%, 30% or 40%.

As used herein, the term "efficiency" means the accuracy with which a method diagnoses a disease state. Efficiency is calculated as the sum of the true positives and true negatives divided by the total number of sample results, and is affected by the prevalence of the trait in the population analyzed. The cut-off values can be selected such that the efficiency of a method of the invention in a patient population having a prevalence of 15% is at least about 45%, and can be, for example, at least about 50%, 55% or 60%.

For determination of the cut-off level, receiver operating characteristic (ROC) curve analysis can be used. In some embodiments, the cut-off value for the classifier can be determined as the value that provides specificity of at least 90%, at least 80% or at least 70%.

Computer Implemented Embodiments

Information from the TP53RK levels and other test results can implemented in computer programs executed on programmable computers that include, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Method of Treatment Using Inhibitors of TPR53K

Also provided are methods for inhibiting proliferation or migration of a multiple myeloma cell to a subject having multiple myeloma or a precursor condition of multiple myeloma by administering a therapeutic agent in an amount effective to inhibit proliferation or migration of the multiple myeloma cell.

In various embodiments, the cells are provided in vitro, in vivo, or ex vivo.

In some embodiments, the therapeutic agent encodes a TP53RK shRNA or siRNA.

In some embodiments, the shRNA is specific for the target sequence CAGTCCACTATGGAGACTGAA (SEQ ID NO:5).

In some embodiments, the therapeutic agent is a TP534K siRNA, e.g., one or more of the following sequences: TP53RK J-003108-09 (SEQ ID NO:6); TP53RK J-003108-10 (SEQ ID NO:7); TP53RK J-003108-11 (SEQ ID NO:8); and/or TP53RK J-003108-12 (SEQ ID NO:9).

Pharmaceutical Preparations of Inhibitory TP53RK Nucleic Acids

Pharmaceutical compositions comprise an effective amount aTP53RK inhibitory RNA (including the shRNA and siRNA disclosed herein), or an agent that increases levels or activity of TP53RK RNA, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one composition will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity (e.g., a purity sufficient for administering the composition to a human subject) standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compositions may be contained in different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further, the composition can be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the composition is provided in a pharmaceutical lipid vehicle composition that includes an agent that increases TP53RK inhibitory RNA levels and an aqueous solvent. As used herein, the term "lipid" is defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

The artisan can use techniques known in the art to disperse a composition of the invention in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes. In specific embodiments, the composition is administered to an individual in a liposome.

The actual dosage amount of a composition administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary TP53RK Inhibitory RNA Compositions and Formulations

In some embodiments, the compositions are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, compositions for delivering an agent that increases TP53RK inhibitory RNA or activity are administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration may also include a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid or liquid particles dispersed in a liquefied or pressurized gas propellant. The typical aerosol for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

The TP53RK inhibitory RNA compositions can be combined with other treatment strategies, i.e., autologous stem cell transplantation and allogeneic effector cell transplantation, to develop an effective treatment strategy based on the stage of myeloma being treated (see, e.g., Multiple Myeloma Research Foundation, Multiple Myeloma: Stem Cell Transplantation 1-30 (2004); U.S. Pat. Nos. 6,143,292, and 5,928, 639, Igarashi, et al. Blood 2004, 104(1): 170-177, Maloney, et al. 2003, Blood, 102(9): 3447-3454, Badros, et al. 2002, J. Clin. Oncol., 20:1295-1303, Tricot, et al. 1996, Blood, 87(3):1196-1198; the contents of which are incorporated herein by reference).

The effectiveness of TP53RK inhibitory RNA multiple myeloma treatment can be assessed using methods known in the art. The staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value <2.0 mg/dL) and B (abnormal renal function, creatinine value.gtoreq.2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta$_2$-microglobulin (β$_2$-M) and albumin, which separates patients into three prognostic groups irrespective of type of therapy.

Administration of the pharmaceutical compositions at selected dosage ranges and routes typically elicits a beneficial response as defined by the European Group for Blood and Marrow transplantation (EBMT) in Table 1, below (taken from U.S. Pat. No. 8,632,772). Table 1 lists the EBMT criteria for response:

TABLE 1

EBMT/IBMTR/ABMTR[1] Criteria for Response

| | |
|---|---|
| Complete Response | No M-protein detected in serum or urine by immunofixation for a minimum of 6 weeks and fewer than 5% plasma cells in bone marrow |
| Partial Response | >50% reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/or >25% increase in bone marrow plasma cells (at least 10% in absolute terms)[2] |
| Relapse | Reappearance of disease in patients previously in complete response, including detection of paraprotein by immunofixation |

[1]EBMT: European Group for Blood and Marrow transplantation; IBMTR: International Bone Marrow Transplant Registry; ABMTR: Autologous Blood and Marrow Transplant Registry.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the composition elicits a response in an individual clinically manifesting at least one symptom associated with MM, depends in part, on the severity of disease, e.g., Stage I, II, or III, and in part, on whether the patient is newly diagnosed or has late stage refractory MM. Thus, in some embodiments, administration of the pharmaceutical composition elicits a complete response.

In some embodiments, administration of the pharmaceutical composition elicits a very good partial response or a partial response. In other embodiments, administration of the pharmaceutical composition elicits a minimal response. In other embodiments, administration of the pharmaceutical composition prevents the disease from progressing, resulting in a response classified as "no change" or "plateau" by the EBMT.

Combination Treatments

An agent that increases TP53RK inhibitory RNA levels can be administered along with an additional therapy or therapies for treating multiple myeloma. For example, in some embodiments, an agent that increases levels or activity of TP53RK inhibitory RNA is administered following the administration of a second therapeutic agent for treating multiple myeloma. Administration of each member of the combination can be sequential or simultaneous.

For example, an agent that increases levels or activity of TP53RK inhibitory RNA can be administered approximately 0 to 60 days after the administration of another therapeutic agent.

The therapeutic agents can be administered in any manner found appropriate by a clinician and are typically provided in generally accepted efficacious dose ranges, such as those described in the Physician Desk Reference, 56th Ed. (2002), Publisher Medical Economics, New Jersey. In other embodiments, a standard dose escalation can be performed to identify the maximum tolerated dose (MTD) (see, e.g., Richardson, et al. 2002, Blood, 100(9):3063-3067, the content of which is incorporated herein by reference).

In some embodiments, doses less than the generally accepted efficacious dose of a therapeutic agent can be used. For example, in various embodiments, the composition comprises a dosage that is less than about 10% to 75% of the generally accepted efficacious dose range. In some embodiments, at least about 10% or less of the generally accepted efficacious dose range is used, at least about 15% or less, at least about 25%, at least about 30% or less, at least about 40% or less, at least about 50% or less, at least about 60% or less, at least about 75% or less, and at least about 90%.

The therapeutic agents administered in a combination treatments can be administered in the same or different routes, i.e., each or both can be administered orally, intravenously, systemically by injection intramuscularly, subcutaneously, intrathecally or intraperitoneally.

Examples of therapeutic agents that can be used in the compositions described herein include, but are not limited to, dexamethasone, thalidomide, melphalan, prednisone, doxorubicin, doxorubicin HCL liposome injection, bortezomib, lenalidomide, and/or combinations thereof.

Accordingly, in some embodiments, two pharmaceutical compositions are provided: a first comprising a therapeutically effective amount of an agent that increases levels or activity of TP53RK inhibitory RNA and a second comprising a therapeutically effective amount of lenalidomide.

In some embodiments, two pharmaceutical compositions are provided: a first comprising a therapeutically effective amount of an agent that increases levels or activity of TP53RK inhibitory RNA and a second comprising a therapeutically effective amount of bortezomib. In some embodiments, at least two pharmaceutical compositions are provided: a first comprising a therapeutically effective amount of an agent that increases levels or activity of TP53RK inhibitory RNA; and a second comprising a therapeutically effective amount of lenalidomide and a therapeutically effective amount of bortezomib. In some embodiments, lenalidomide and bortezomib are provided separately, such that a total of three pharmaceutical compositions are provided: a first comprising an agent that increases levels or activity of TP53RK inhibitory RNA, a second comprising lenalidomide, and a third comprising bortezomib.

In some embodiments, at least two pharmaceutical compositions are provided: a first comprising a therapeutically effective amount of an agent that increases levels or activity of TP53RK inhibitory RNA, and a second comprising a therapeutically effective amount of lenalidomide and dexamethasone. In some embodiments, lenalidomide and dexamethasone are provided separately, such that a total of three pharmaceutical compositions are provided: a first comprising an agent that increases levels or activity of TP53RK inhibitory RNA, a second comprising lenalidomide, and a third comprising dexamethasone.

In some embodiments at least two pharmaceutical compositions are provided: for example, a first comprising a therapeutically effective amount of an agent that increases levels or activity of TP53RK inhibitory RNA, and a second comprising a therapeutically effective amount of bortezomib and dexamethasone. In some embodiments, bortezomib and dexamethasone are provided separately, such that a total of three pharmaceutical compositions are provided: a first comprising an agent that increases levels or activity of TP53RK inhibitory RNA, and a second comprising bortezomib, and a third comprising dexamethasone.

In some embodiments, at least two pharmaceutical compositions are provided: a first comprising a therapeutically effective amount of an agent that increases levels or activity of TP53RK inhibitory RNA, and a second comprising therapeutically effective amount of lenalidomide, bortezomib, and dexamethasone. In some embodiments, lenalidomide, bortezomib, and dexamethasone are provided separately. Provided that the agents retain their efficacy, compositions comprising other combinations can be prepared, depending in part, on dosage, route of administration, and whether the agents are provided in a solid, semi-solid or liquid form. For example, a total of three compositions can be made: a first comprising a therapeutically effective amount of an agent that increases levels or activity of TP53RK inhibitory RNA, a second comprising dexamethasone, and a third comprising lenalidomide and bortezomib.

In some embodiments, at least two pharmaceutical compositions are provided: a first comprising a therapeutically effective amount of an agent that increases levels or activity of TP53RK inhibitory RNA, and a second comprising a therapeutically effective amount of bortezomib and optionally can comprise one or more of the following agents: thalidomide, dexamethasone, melphalan, doxorubicin, doxorubicin HCl liposome injection, and/or prednisone. Provided that the TP53RK inhibitory RNA agents retain their efficacy, compositions comprising various combinations of thalidomide, dexamethasone, melphalan, doxorubicin, doxorubicin HCl liposome injection, and prednisone can be prepared depending in part, on dosage, route of administration, and whether the agents are provided in a solid, semi-solid or liquid form.

Also provided is a kit for prognosing, diagnosing, staging or monitoring the progression of multiple myeloma in a patient. The kit includes a reagent that specifically detects a TPR53K polypeptide and/or a TPR53K RNA and is useful for measuring TP53RK protein levels or transcripts. The agents can be provided in a concentrated or lyophilized form with a diluent for resuspension. The kit optionally includes equipment for using the reagents, e.g., one or more syringes, needles or tubing. Preferably, the kit is suitable for in-office testing of a suitable bodily fluid of a patient. If desired, the kit includes a package for performing one or more TP53RK assays and includes instructions for use in a method or system described herein.

In some embodiments, the reagent is a TPRK53 antibody, e.g., a polyclonal or monoclonal antibody.

In some embodiments, the kit includes reagents for performing an ELISA assay.

In some embodiments, the kit includes reagents for performing a lateral flow assay.

In some embodiments, the kit includes a reagent with one or more nucleic acids that specifically bind to a TRP53RK nucleic acid.

Screening for Therapeutic Agents for Treating a Hematological Malignancy

To identify therapeutic agents for treating multiple myeloma, a test agent is screened for its ability to lower the expression or activity of TP53RK in multiple myeloma cells.

For example, a method for identifying an agent for treating multiple myeloma (MM) or other hematological malignancies includes providing a first polypeptide comprising a test agent polypeptide under conditions that allow for binding of the TP53RK polypeptide and the test agent. The complex is then assayed to determine whether the test agent disrupts activity or expression of TP53RK. Decreased expression or activity of TP53RK in the presence of the test agent indicates the test agent is a potential therapeutic agent for treating MM.

The TP53RK sequences used in the screening methods can include, e.g., TP53RK polynucleotide and polypeptide sequences known in the art. Thus, in some embodiments, TP53R (TP53RK polypeptide-encoding sequences extend from polynucleotide 224 to 985 of SEQ ID NO:1, NCBI Reference Sequence: NM_033550.3):

A test agent that decreases activity or expression of TP53RK can be further characterized to determine its suitability as a therapeutic agent for treating MM. For example, a promising test agent can be further characterized to determine whether it inhibits proliferation of an MM cell population and/or whether it inhibits migration of MM cells into bone marrow. Inhibition of MM cell proliferation and/or migration indicates the test agent is a therapeutic agent for treating MM.

In some embodiments, the candidate agent is further screened to determine its effect on hTERT and/or p53.

In some embodiments, screening is performed in the presence of cells expressing aP53RK binding protein (TPRKB), e.g., in a cell expressing the polypeptide endogenously or in a cell engineered to express TPRKB.

In some embodiments, a TPRKB polypeptide sequence includes the amino acid sequence of SEQ ID NO:3, as well as a polynucleotide sequence of SEQ ID NO:4, which encodes the polypeptide (from *Homo sapiens* TP53RK binding protein (TPRKB), mRNA NCBI Reference Sequence: NM_016058.2):

Test Agents

The term "test agent" or "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of disregulation of apoptosis in a cell or tissue). Test agents comprise both known and potential therapeutic compounds. A test compound can be determined to be therapeutic by using the screening methods of the present invention.

The screening methods can include those known or used in the art or those first described herein. For example, in one embodiment a TP53RK polypeptide is immobilized on a microtiter plate and incubated with a test agent. Subsequently, the complex is detected using a secondary antibody, and absorbance can be detected on a plate reader.

The test agent can be a small molecule or a large molecule. A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

A test agent can be compared to the a known therapeutic compound for its efficacy in treating multiple myeloma. A "known therapeutic compound" refers to a therapeutic compound that has been shown (e.g., through animal trials or prior experience with administration to humans) to be effective in such treatment or prevention.

The test agent need not be any particular structure or size. In some embodiments, the test agent is a nucleic acid, a polypeptide, a small molecule or combinations thereof, an inhibitory nucleic acid, e.g., a triplex forming oligonucleotide, an aptamer, a ribozyme, an antisense RNA, a short interfering RNA (siRNA), or a micro-RNA (miRNA).

In some embodiments, the polypeptide is a polypeptide binding partner of a TP53RK polypeptide.

For example, the polypeptide can be an antibody or an intrabody form of an antibody. An intrabody is an antibody that functions within a cell to bind to an intracellular protein.

Antibodies are preferably modified to reduce the likelihood of an unwanted host reaction. One example of such a modification is a humanized antibody. Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., Nature, 321:522-525 (1986); Riechmann et al., Nature 332:323-327 (1988); Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using other techniques known in the art, including phage display libraries (Hoogenboom and Winter, J. Mol. Biol., 227:381 (1991); Marks et al., J. Mol. Biol., 222:581 (1991)). The techniques of Cole and Boerner are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

In addition, TP53RK antibodies can be used to create a therapeutic agent for treating MM, or another disease by adapting methods for making humanized antibodies described in U.S. Pat. No. 8,673,593. The method includes providing a DNA encoding the variable domains of a donor TP53RK antibody and determining the amino acid sequence of the CDR regions of the donor monoclonal antibody from the DNA, selecting human acceptor antibody sequences; and producing a humanized TP53RK antibody comprising the CDRs from the donor antibody and variable region frameworks from the human acceptor antibody sequences. If desired, the method can further include determining whether a humanized antibody disrupts binding of a first polypeptide comprising TP53RK and a second polypeptide, such as a TPRKB under conditions that allow for binding of the TPRKB polypeptide and TP sequence. Disruption of the binding of the first polypeptide and second polypeptide by the humanized antibody indicates it is a therapeutic agent for treating MM.

The antibody preferably binds specifically (or selectively) to a TP53RK molecule. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

If desired, the antibody can be provided conjugated or coupled to a detectable label, a radioactive label, an enzyme, a fluorescent label, a luminescent label, a bioluminescent label, or a therapeutic agent.

Assays for identifying TP53RK inhibitors can be performed in either a cell-free or a cell-based system. Art recognized methods for measuring protein-protein interactions can be used to characterize binding of the TP53RK polypeptide and the test agent, for example, by coupling the test agent with a radioisotope or enzymatic label such that binding of the test compound to the antigen or biologically-active portion thereof can be determined by detecting the labeled compound in a complex. For example, test agents can be labeled with $^{125}I$, $^{35}S$, $^{14}C$, or $^{3}H$, either directly or indirectly, and the radioisotope detected by direct counting of radioemission or by scintillation counting. Alternatively, test agents can be enzymatically-labeled with, for example, horseradish peroxidase, alkaline phosphatase, or luciferase, and the enzymatic label detected by determination of conversion of an appropriate substrate to product.

In one embodiment, the assay comprises contacting the TP53RK polypeptide complex with a test agent, and determining the ability of the test compound to interact with the complex or otherwise disrupt the existing complex. In this embodiment, determining the ability of the test compound comprises determining the ability of the test compound to preferentially bind to TP53RK or a biologically-active portion thereof, as compared to its binding partner.

Observation of the complex in the presence and absence of a test agent can be accomplished in any vessel suitable for containing the reactants. Examples of such vessels include microtiter plates, test tubes, and micro-centrifuge tubes. In one embodiment, a fusion protein that adds a domain that allows one or both of the proteins to be bound to a matrix can be provided. In one embodiment, GST-antibody fusion proteins or GST-antigen fusion proteins are adsorbed onto glutathione Sepharose® beads (Sigma Chemical, St. Louis, Mo.) or glutathione-derivatized microtiter plates, that are then combined with the test compound, and the mixture is incubated under conditions conducive to complex formation (e.g., at physiological conditions for salt and pH).

Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

In some embodiments, the TP53RK sequence is immobilized to facilitate separation of complexed from uncomplexed forms of one or both following introduction of the rest agent, as well as to accommodate automation of the assay. If desired, either member of the putative complex can be immobilized utilizing biotin and streptavidin. Biotinylated antibody or antigen molecules can be prepared from biotin-NHS (N-hydroxysuccinimide) using techniques well-known in the art (e.g., biotinylation kit, Pierce Chemicals, Rockford, Ill.), and immobilized in the wells of streptavidin-coated 96 well plates (Pierce Chemical). Methods for detecting such complexes, in addition to those described above for the GST-immobilized complexes, include immunodetection of complexes using such other antibodies reactive with the antibody or antigen.

In some embodiments, binding of the test agent to the complex is detected using assay AlphaScreen® technology (PerkinElmer, Waltham, Mass.).

Cells Used in Screening

In general, any cell that expresses or can be engineered to express TP53RK in detectable amounts can be used in the screening assays described herein. When cell-based assays are used, TP53RK expressing cells can be provided by any cell (e.g., MM1S, OPM1, H929, U266 cells) that expresses TP53RK and, preferably TPRKB, in amounts sufficient to be detected. The cell can be provided in vitro, in vivo or ex vivo, and can be prokaryotic or eukaryotic, for example, mammalian cells including both human and non-human mammalian cells (e.g., a rodent such as a mouse or rat cell).

Cells can be primary cells or established cell lines. In some embodiments hematopoietic cells are used. The term "hemapoietic cells" as used herein includes all blood cell types, including those from the myeloid lineage (monocytes and macrophages, neutrophils, basophils, eosinophils, erythrocytes, megakaryocytes/platelets, dendritic cells), and lymphoid lineages (T-cells, B-cells, NK-cells).

In some embodiments, cells produce or are engineered to produce high levels of TP53RK transcripts and/or proteins, see, e.g., WO2013/089278.

A "sample" in the context of screening assays is understood within the scope of the invention to refer to a suitable cell, group of cells, animal model or human. These samples do not have to be derived from a subject. A sample in this context can be a group of cells from a cell line. Preferably cell lines are derived from a hematopoietic disorder. A non-limiting list of samples includes bone marrow aspirates or bone marrow biopsy (for myeloma, leukemias and other hematopoietic disorders), lymph node samples (for lymphomas and other hematopoietic disorders) and peripheral blood samples (for leukemias and other hematopoietic disorders). The sample may be of a particular type of hematopoietic cell, for example a population of B lymphocytes and/or T lymphocytes.

Detecting TP53RK Polypeptides and Transcripts

The presence and/or level of TP53RK proteins used in the screening methods described herein can be evaluated using methods known in the art, e.g., using quantitative immunoassay methods such as enzyme linked immunosorbent assays (ELISA), immunoprecipitations, immunofluorescence, enzyme immunoassay (EIA), radioimmunoassay (RIA), and Western blot analysis.

Similarly, the presence and/or level of transcripts encoding TP53RK proteins can be evaluated using RNA detection methods known in the art, e.g., quantitative transcription detection such as a transcription-based amplification system (TAS). Some examples of RNA detection systems include PCR and QRT-PCR-based amplification systems, ligase chain reaction, Qβ replicase, reverse transcriptase-coupled nucleic acid sequence-based amplification (NASBA), self-sustained sequence replication (3SR), strand displacement amplification (SDA), or reverse transcriptase-coupled rolling circle amplification (RCA).

In some embodiments, a machine-readable storage medium can comprise a data storage material encoded with machine readable data or data arrays which, when using a machine programmed with instructions for using the data, is capable of use for a variety of purposes, such as, without limitation, subject information relating to a diagnosing multiple myeloma, or evaluating the effectiveness of a treatment (e.g., surgery or chemotherapy).

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein.

The health-related data management system of the invention may also be considered to be implemented as a computer-readable storage medium, configured with a computer program, where the storage medium so configured causes a computer to operate in a specific and predefined manner to perform various functions described herein.

The invention will be further illustrated in the following non-limiting examples. The examples show that immunodulatory drugs (IMiDs) thalidomide and lenalidomide trigger anti-multiple myeloma (MM) activity by binding to cereblon (CRBN), facilitating proteasomal degradation of IKZF1/3. We show that pomalidomide binds not only to CRBN, but also to p53-related protein kinase (TP53RK), thereby blocking its activity. TP53RK knockdown in MM: inhibits p53; decreases MDM2 and downstream XIAP, with E2F dependent Bim activation, mediating apoptotic and autophagic cell death; and downregulates c-Myc and its target IKZF1/3. IMiDs therefore regulate IKZF1/3 expression via CRBN and proteasomal degradation, as well as transcriptional inhibition of cMyc via TP53RK-p53 axis. TP53RK knockdown also identified novel interacting proteins ribonucleotide reductase, p18CDKN2C, and telomerase reverse transcriptase. These examples therefore both define novel molecular mechanisms of IMIDs-mediated anti-MM activity and identify novel potential therapeutic targets in MM.

Figure 22:
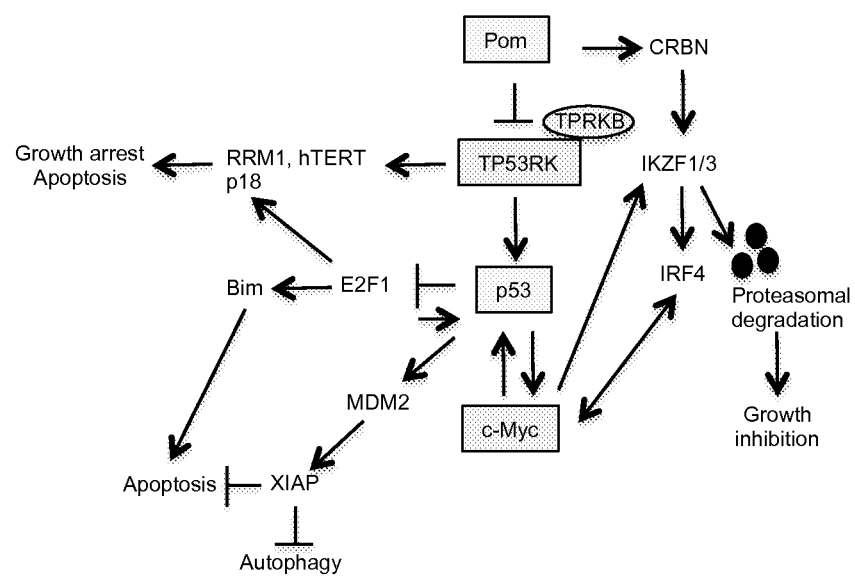
FIG. 22 is a drawing showing a proposed mechanism whereby IMiDs and/or TP53RK inhibition trigger anti-MM activity.

The results discussed in the following examples not only delineate a novel mechanism of action whereby IMIDs inhibit TP53RK and induce autophagic and apoptotic MM cell death, but also identify and validate TP53RK as promising therapeutic target in MM. p53 is a known tumor suppressor, and our studies demonstrate that IMiDs inhibit p53 activity (FIG. 22). Moreover, our demonstration that IMiDs also inhibit expression of hTERT, a key regulator of genomic stability, may underly the predisposition to secondary cancers observed in patients treated with IMiDs in combination with DNA damaging agents including melphalan.

Example 1. General Materials and Methods

Cells

MM.1S and MM.1R cell lines were kindly provided by Dr. Steven Rosen (Northwestern University, Chicago, Ill.). NCI-H929 (H929), RPMI8226, and U266 cells were obtained from American Type Culture Collection (Manassas, Md.). Doxorubicin-resistant RPMI-Dox40 cell line was provided by Dr. William Dalton (H Lee Moffitt Cancer Center, Tampa, Fla.). OPM1 and OPM2 were provided from Dr. P. Leif Bergsagel (Mayo Clinic, Tucson, Ariz.). All MM cells were cultured in RPMI1640 medium. HEK-293FT cells were obtained from Invitrogen (Grand Island, N.Y.) and maintained in DMEM medium. All media were supplemented with 10% fetal bovine serum, 100 U/mL of penicillin, and 100 ug/mL of streptomycin.

Patient MM cells were purified from bone marrow (BM) aspirates by negative selection (RosetteSep Separation System®, StemCell Technologies, Vancouver, Canada). The purity of MM cells (>85%) was confirmed by flow cytometric analysis using anti-CD138 Ab (BD Pharmingen, San Diego, Calif.), as in prior studies. All experiments with patient samples were performed under auspices of an DFCI Institutional Review Board approved protocol.

Reagents and Antibodies

Thalidomide (Thal), lenalidomide (Len), pomalidomide (Pont), and MDM2 inhibitor Nutlin-3a were purchased from Selleck Chemicals (Houston, Tex.). E2F inhibitor HLM006474 was obtained from EMD Millipore (Darmstadt, Germany). TAS-116 was provided by TAIHO PHARMACEUTICAL CO., LTD (Ibaraki, Japan). Anti-FLAG M2-agarose beads were purchased from Sigma. Anti-p53 and -nucleolin (C23), -actin and -MDM2 Abs were purchased from Santa Cruz Biotechnology (Santa Cruz, Calif.); anti-TP53RK (PRPK) and -CRBN Abs were obtained from Sigma, and anti-TPRKB and -RRM1 Abs were from Abcam (Cambridge, Mass.). All other Abs used were purchased from Cell Signaling Technologies (Danvers, Mass.). For detection of TP53RK-Myc DDK and TPRKB-Myc-DDK, infrared imaging system (LI-COR, Lincoln, Nebr.) was employed using anti-mouse IRDye 680RD/LiCor/926-68070 (red color) and anti-rabbit IRDye 800CW/LiCor/926-32211 (green color) secondary Abs.

Growth Inhibition Assay

Cell growth was assessed by measuring 3-(4,5-dimethylthiazol-2-yl)-2,5-diphenyl tetrasodium bromide (MTT, Chemicon International, Temecula, Calif.) dye absorbance. Cells were pulsed with 10 µl of 5 mg/ml MTT to each well for the last 4 h of 48 h and/or 72 h cultures, followed by 100 µl isopropanol containing 0.04N HCl. Absorbance was measured at 570/630 nm using a spectrophotometer (Molecular Devices Corp., Sunnyvale Calif.).

Preparation of Affinity Chromatography Reagents

Based on prior studies[1] and our functional data, the 3' position of pomalidomide was selected for attachment to affigel-10 to generate the active affinity reagent (pomalidomide-based). The activities of 3'-methyl derivative is similar to those of pomalidomide in assays of B cell growth inhibition and co-stimulation of IL-2 production, supporting the assumption that attachment to a solid support through the 3' position does not perturb target binding. A 3'-n-butylamine derivative of pomalidomide was synthesized and attached to the solid support via linker to generate the pomalidomide-based affinity reagent. Affi-Gel 10 obtained from Bio-Rad was incubated with pomalidomide derivative and triethylamine in dimethylsulfoxide for 4 h at 4° C. Any unreacted residues that remain were blocked by addition of ethanolamine at the end of the reaction, and the resulting affinity reagents were stored in isopropanol at −20° C. Thalidomide-based reagent was synthesized according to a previous report (Ito et al. Science, 2010).

Affinity Purification with Pomalidomide-Based Reagents

Standard affinity chromatography was performed to identify proteins that bind specifically to pomalidomide-based affinity reagents. Cell lysates from HEK-293FT cells were prepared in NP-40 lysis buffer [(0.4% NP-40, 50 mM HEPES (pH 7.5), 150 mM NaCl, 1.5 mM MgCl2, 1 mM DTT, 1 mM Na3VO4, 25 mM NaF, protease inhibitor mix (Roche)] at approximately $5 \times 10^7$ cells per mL (10 mg protein/mL) at 4° C. The lysates were incubated for 30 min on ice, preformed freeze-thawed twice, and centrifuged at 2,000 g for 10 min. The pellets were discarded, and the supernatants were then centrifuged at 800 g for 5 min. The supernatants were collected and then ultracentrifuged at 100,000 g for an hour. The resulting supernatants were used in the affinity chromatography assay immediately.

Pomalidomide-based affinity reagent and control reagent were equilibrated with NP-40 lysis buffer. After pre-cleaning the lysates with a control reagent (ethanolamine-affigel) to reduce non-specific binding, the lysates were incubated with either the ethanolamine-affigel or pomalidomide-based affinity reagent (80 uL of each, 50% slurry) for an hour at 4° C. to identify candidate binding proteins. In competition assays, 10-fold excess pomalidomide or thalidomide was added to lysate from pomalidomide-based or thalidomide-based affinity reagents, respectively Affinity reagents were washed three times with NP-40 lysis buffer, and binding proteins were then eluted with 2×SDS sample buffer at 50° C. The eluted samples were subjected to 4-20% SDS-PAGE for silver staining and mass spectrometry analysis, as well as immunoblotting. Mass Spectrometry was carried out at the Taplin Mass Spectrometry Facility at Harvard Medical School (Boston, Mass.).

Recombinant TP53RK and TPRKB

Full-length TP53RK and TPRKB sequences obtained from OriGene (Rockville, Md.) were cloned and inserted into pCMV6-AC-Myc-DDK. These constructs were transiently transfected into HEK-293FT cells to overexpress recombinant C-terminal Myc-DDK tagged TP53RK and TPRKB by calcium phosphate transfection. The recombinant proteins were immunoprecipitated with anti-DDK agarose beads and subjected to gel chromatography using Superdex 200 sizing column with an HPLC system. TP53RK and TPRKB proteins were co-eluted in the same fraction, whereas the TPRKB single protein was eluted in later fractions.

In Vitro Auto-Phosphorylation Assay

In vitro TP53RK auto-phosphorylation assay was performed as previously described[2]. Briefly, purified recombinant TP53RK and TPRKB proteins (1.5-3 μg/reaction) were incubated with 25 uM [γ-32P]ATP (3000 Ci/mmol, 10 mCi/mL, PerkinElmer, Boston, Mass.) in HEPES buffer (25 mM HEPES (pH 7.5), 100 mM NaCl, 25 mM $MgCl_2$. 2 mM DTT, phosphatase inhibitor mix (Roche) for 30 min at 30° C. The reaction was terminated by adding SDS sample buffer, and reaction mixtures were subjected to SDS-PAGE and autoradiography, as well as Coomassie blue staining.

Immunoblotting and Silver Staining

MM cells were harvested and lysed using RIPA-lysis buffer (Boston Bioproducts, Ashland, Mass.) containing 5 mM EDTA, 5 mM NaF, 2 mM Na3VO4, 1 mM PMSF, 5 μg/ml leupeptin, and 5 μg/ml aprotinin. Nuclear proteins were extracted using "Nuclear Extraction Kit" (Affimetrix). After the determination of protein concentration using DC protein assay (Bio-Rad, Hercules, Calif.), β-mercaptoethanol (-ME) was added to the whole-cell lysates to a 2% final concentration. The whole cell lysates or nuclear extracts were subjected to SDS-PAGE, transferred to nitrocellulose membranes (Bio-Rad, Hercules, Calif.) or polyvinylidene fluoride membranes (Millipore, Billerica, Mass.), and immunoblotted with indicated Abs. Silver staining was carried out using "SilverQuest Staining Kit®" (Invitrogen), according to manufacturer's protocol.

RNA Extraction and Reverse Transcription Polymerase Chain Reaction

RNA was extracted using Trizol (Invitrogen) and quantified by a Nanodrop spectrophotometer (Labtech). Specifically, 5×10[6] cells were pelleted, washed with cold PBS, and resuspended in 1 mL Trizol. They were then incubated with 1-Bromo-3-chloropropane (Sigma), washed first with Iso-propyl alcohol and then with 75% Ethanol, and resuspended in Nuclease Free-water (Invitrogen). After quantification, 2000 ng of RNA was used to synthesize cDNA via the Superscript II First strand synthesis Kit (Invitrogen), according to the manufacturer's instructions. To evaluate the expression levels of TP53RK, BCL2L11, MYC, Bim, E2F1, TP53, IKZF1, IKZF3, RRM1, p18CDKN2C, PSMB5, PSMB7, PSMA3 and GAPDH, quantitative real time PCR (QRT-PCR) was performed using SYBR GREEN PCR Master Mix (Applied Biosystem), after optimization of the primer conditions. cDNAs were diluted 1:100 or 1:1000 and amplified in a 20 μL reaction. Primers were used at 200 nM or 400 nM concentration. Primers used in this study are listed in Table 2 below. Thermal cycling conditions were: 10 minutes at 95° C., 40 cycles at 95° C. for 15 seconds, followed by 1 minute at 60° C. Real-time quantitative PCR was performed on ABI Prism 7300 Sequence Detection System (Applied Biosystems). Data were analyzed using the delta delta Ct method. GAPDH was used as an invariant control.

TABLE 2

| Target genes | Directions | Sequences |
|---|---|---|
| TP53 | Forward | CCCAAGCAATGGATGATTTGA (SEQ ID NO: 10) |
| | Reverse | GGCATTCTGGGAGCTTCATCT (SEQ ID NO: 11) |
| BCL2L11 | Forward | GGCCCCTACCTCCCTACA (SEQ ID NO: 12) |
| | Reverse | GGGGTTTGTGTTGATTTGTCA (SEQ ID NO: 13) |
| E2F1 | Forward | ATGTTTTCCTGTGCCCTGAG (SEQ ID NO: 14) |
| | Reverse | ATCTGTGGTGAGGGATGAGG (SEQ ID NO: 15) |
| MYC | Forward | TTTTTCGGGTAGTGGAAA (SEQ ID NO: 16) |
| | Reverse | GCAGTAGAAATACGGCTGCAC (SEQ ID NO: 17) |
| TP53RK | Forward | TGGCTCGAATGCACGATGAAG (SEQ ID NO: 18) |
| | Reverse | TGAAACTCAGCCCAAAGTCTATG (SEQ ID NO: 19) |
| IKZF1 | Forward | TTCCGTGATCCTTTTGAGTGC (SEQ ID NO: 20) |
| | Reverse | CTCGCGTTATGTGCGACGA (SEQ ID NO: 21) |
| IKZF3 | Forward | GCTCATACAGACCCGCATGAT (SEQ ID NO: 22) |
| | Reverse | AACTGGAACCATCTCCGAGGT (SEQ ID NO: 23) |
| GAPDH | Forward | GAAGGTGAAGGTCGGAGTCA (SEQ ID NO: 24) |
| | Reverse | GGGGTCATTGATGGCAACAATA (SEQ ID NO: 25) |
| RRM1 | Forward | ACTTCGGCTTTAAGACGCTAGA (SEQ ID NO: 26) |
| | Reverse | GCATGAGTAAACCACCTCTCAGA (SEQ ID NO: 27) |
| CDKN2C | Forward | GGGGACCTAGAGCAACTTACT (SEQ ID NO: 28) |
| | Reverse | CAGCGCAGTCCTTCCAAAT (SEQ ID NO: 29) |
| PSMB5 | Forward | AGGAACGCATCTCTGTAGCAG (SEQ ID NO: 30) |
| | Reverse | AGGGCCTCTCTTATCCCAGC (SEQ ID NO: 31) |

TABLE 2-continued

| Target genes | Directions | Sequences |
|---|---|---|
| PSMB7 | Forward | TTTCTCCGCCCATACACAGTG (SEQ ID NO: 32) |
| | Reverse | AGCACCTCAATCTCCAGAGGA (SEQ ID NO: 33) |
| PSMA3 | Forward | GCTCAATCGGCACTGGGTAT (SEQ ID NO: 34) |
| | Reverse | ACCTGCTACTGCCATTCCAAC (SEQ ID NO: 35) |

Lentiviral shRNA Infection and siRNA Transfection pLKO.1-based shRNA vectors were obtained from the RNAi Consortium (Broad Institute). The RNAi Consortium clone ID and target sequence of each plasmid is listed in Table 3. Recombinant lentivirus was produced by transient transfection of 293T cells following a standard protocol. After 48 hours, MM cells were incubated with culture supernatants from 293T cells containing crude virus for 6 hours and washed with media. After 24 h of infection, cells expressing shRNA were selected with puromycin dihydrochloride (Sigma-Aldrich) at 1-2 µg/ml for 48 h, and then examined for proliferation and/or subjected to immunoblotting analysis. For siRNA transfection, scrambled, TP53RK, CRBN, p53, c-Myc and RRM1 siRNAs were purchased from Thermo Scientific (Lafayette, Colo.). siRNA transfection was carried out by Amaxa electroporation system using "Cell Line Nucleofector® Kit V or C" solution (Lonza, Koln, Germany). The sequences of short hairpins and small interference RNA are listed in Table 4.

TABLE 3

| shRNAs | Clone IDs | Target Sequences |
|---|---|---|
| shTP53RK #1 | TRCN0000037522 | CAGTCCACTATGGAGACTAA (SEQ ID NO: 36) |
| shTP53RK #2 | TRCN0000196805 | GAAGACCTCATTCATGGTGAT (SEQ ID NO: 37) |
| shMYC | TRCN0000039642 | CCTGAGACAGATCAGCAACAA (SEQ ID NO: 38) |
| shp53 (A12) | TRCN0000003753 | CGGCGCACAGAGGAAGAGAAT (SEQ ID NO: 39) |
| shp53 (B10) | TRCN0000003756 | CACCATCCACTACAACTACAT (SEQ ID NO: 40) |
| shp53 (D1) | TRCN0000003755 | GTCCAGATGAAGCTCCCAGAA (SEQ ID NO: 41) |
| shp53 (D6) | TRCP0001527933 | GAGGGATGTTTGGGAGATGTA (SEQ ID NO: 42) |
| shp53 (D9) | TRCP0001527933 | TCAGACCTATGGAAACTACTT (SEQ ID NO: 43) |
| shLuc (control) | TRCN0000072246 | CAAATCACAGAATCGTCGTAT (SEQ ID NO: 44) |

TABLE 4

| siRNA | Sequence |
|---|---|
| ON-TARGETplus SMARTpool siRNA TP53RK | |
| J-003108-09, TP53RK | GGUAGAAGAAUGUGUAUGA (SEQ ID NO: 45) |
| J-003108-10, TP53RK | GCUUCCAACUGCUUAUAUA (SEQ ID NO: 46) |
| J-003108-11, TP53RK | GCUGAACAUUGUGCUCAUA (SEQ ID NO: 47) |
| J-003108-12, TP53RK | GUACCCAUCCCAACACUGA (SEQ ID NO: 48) |
| ON-TARGETplus SMARTpool siRNA TP53 | |
| J-003329-14, TP53 | GAAAUUUGCGUGUGGAGUA (SEQ ID NO: 49) |
| J-003329-15, TP53 | GUGCAGCUGUGGGUUGAUU (SEQ ID NO: 50) |
| J-003329-16, TP53 | GCAGUCAGAUCCUAGCGUC (SEQ ID NO: 51) |
| J-003329-17, TP53 | GGAGAAUAUUUCACCCUUC (SEQ ID NO: 52) |
| ON-TARGETplus SMARTpool siRNA MYC | |
| J-003282-26, MYC | CGAUGUUGUUUCUGUGGAA (SEQ ID NO: 53) |
| J-003282-25, MYC | AACGUUAGCUUCACCAACA (SEQ ID NO: 54) |
| J-003282-24, MYC | GAACACACAACGUCUUGGA (SEQ ID NO: 55) |
| J-003282-23, MYC | ACGGAACUCUUGUGCGUAA (SEQ ID NO: 56) |
| ON-TARGETplus SMARTpool siRNA CRBN | |
| J-021086-12, CRBN | CGACUUCGCUGUGAAUUAG (SEQ ID NO: 57) |
| J-021086-11, CRBN | GACAUUACCUCUUCAGCUU (SEQ ID NO: 58) |
| J-021086-10, CRBN | GUAUAAGGCUUGCAACUUG (SEQ ID NO: 59) |
| J-021086-9, CRBN | CAAUUAGAAUCCCUCAAUA (SEQ ID NO: 60) |
| ON-TARGETplus SMARTpool siRNA RRM1 | |
| J-004270-05 RRM1 | UAUGAGGGCUCUCCAGUUA (SEQ ID NO: 61) |
| J-004270-06 RRM1 | UGAGAGAGGUGCUUUCAUU (SEQ ID NO: 62) |
| J-004270-07 RRM1 | UGGAAGACCUCUAUAACUA (SEQ ID NO: 63) |
| J-004270-08 RRM1 | CUACUAAGCACCCUGACUA (SEQ ID NO: 64) |

GEP Analyses

Expression data for plasma cells from healthy donors, monoclonal gammopathy of undetermined significance (MGUS), and smoldering myeloma (SMM) were derived from GSE5900 dataset, while expression data from normal plasma cells and 65 MM patients were obtained from GSE4452 dataset, using expression profiling on Affymetrix GeneChip (t test, unpaired, equal variance). To analyze impact of TP53RK on 170 newly diagnosed patient survival, we used IFM (Intergroup Francophone du Myeloma (IFM) dataset (GSE39754). To relate IKZF1 with MYC levels, the GSE21349 dataset was used, probe sets 205039_s_at for IKZF1 and 202431_s_at for MYC. To relate IKZF1 with TP53RK levels, the GSE21349 dataset was used, probe sets 227346_at for IKZF1 and 202431_s_at for MYC. Linear regression t-test was used to test statistical significance. Basal and after lenalidomide treatment gene expression profiling were obtained from GSE8546 and GSE3142 datasets. In particular, in dataset GSE8546 15 matched patient GEP data before and after lenalidomide-treatment were identified. Data were then normalized and analyzed using D-chip software, seeking statistically significant differences among groups or in p53-target gene expression. Statistical significance was determined by Student t test. The minimal level of significance was P<0.05. Affymetrix U133 Plus 2.0 GEPs data were obtained upon downregulation of TP53RK or treatment with 1 µM lenalidomide or pomalidomide in H929 cells. Gene set enrichment analysis (GSEA) was performed as previously described (2) (GSEA v2.0 at http://www.broad.mit.edu/gsea) using gene set as permutation type, as well as 1,000 permutations and signal to noise as metrics for ranking genes.

ChIP-Seq Data Analysis

ChIP-Seq dataset was downloaded from GSE36354[3]. According to study design, MM.1S MYC and background data downloaded from SRA before preprocessing. SRAToolkit was used for converting SRA file to fastq files, and reads quality was checked before alignment with FASTQC tool. All reads were aligned with Bowtie (version 1.0.0) to the hg19 genome by allowing 2 mismatches and without allowing multiple locations. MACS (version 2.0.10.20131216) was used to identify regions of ChIP-Seq enrichment over background. In order to display c-Myc binding at ±5 kb around the transcription start site (TSS), we used IGV (version 2.3.32)[7] tool and normalized coverage data per million reads.

Transcription Factor DNA Binding Activity

E2F1 DNA binding activity was assessed by electrophoretic mobility shift assay (EMSA) using "EMSA Gel Shift Kit®" from Affimetrix (Santa Clara, Calif.), and p53 DNA binding activity was performed using "p53 Transcription Factor Assay Kit®" from Cayman Chemical (Ann Arbor, Mich.). Experiments were carried out according to manufacturer's protocols.

Proteasome Activity Assay

Proteasome activity was measured by using Proteasome-Glo™ chymotrypsin-like cell-based assay (Promega, Madison, Wis.) according to manufacturer's protocol.

Detection of Telomerase Activity

Telomerase activity in MM.1S and H929 cells was assessed by "TeloTAGGG Telomerase PCR ELISA®" from Roche Applied Science (Mannheim, Germany).

Statistical Analysis

Statistical significance of differences observed in drug-treated versus control cultures was determined using the Wilcoxon signed-ranks test or student t-test. The minimal level of significance was p<0.05.

Example 2. iMIDs Function by Inhibiting TP53RK

Figure 6:
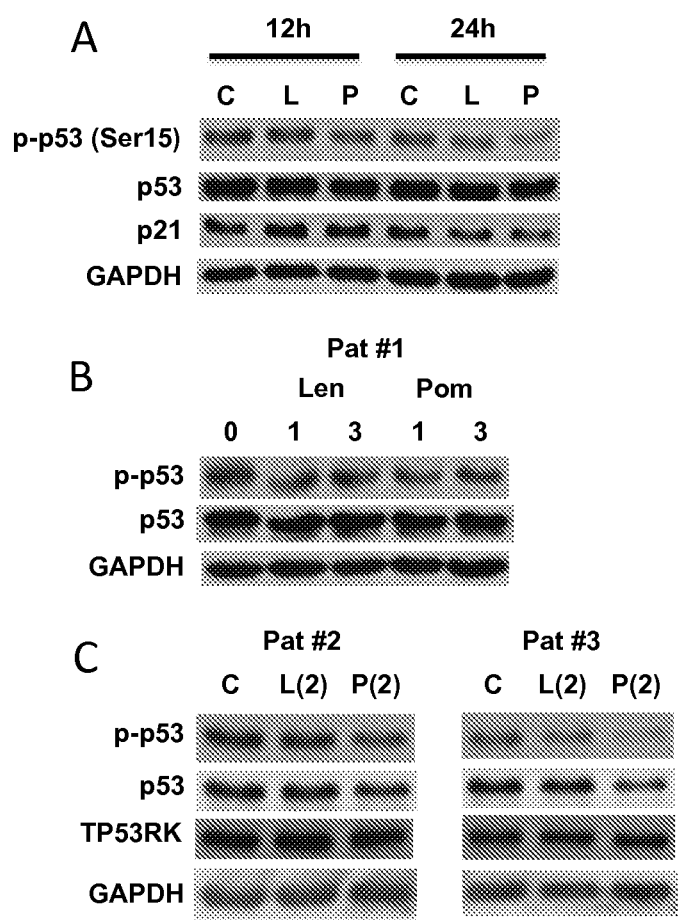
FIGS. 6A-C are Western blots showing inhibition of phosphorylation of p53 by IMiDs in (A) MM.1S cells and patient MM cells (B, C).

In patient MM cells, p53 target genes are altered when treated with Len (Table 5). We first showed that MM.1S and NCI-H929 (H929) cells with wt-p53 are more sensitive to Len and pomalidomide (Pom) than cell lines with mutant (mt)-p53 (FIG. S1). In MM.1S cells both phosphorylated (p-Ser15)-p53 and p53 are downregulated by Len or Pom treatment (FIG. 1A), more potently by Pom than Len (FIG. 6A). This downregulation is further confirmed in nuclear extracts from MM.1S and H929 cell lines (FIG. 1B) as well as in patient MM cells (FIGS. 6B-C).

Consistent with downregulation of p-p53, Len and Pom also block p53 activity in MM.1S and H929 cells (FIG. 1C). Since p53 is phosphorylated at several serine residues, we assessed phosphorylation at Ser20 and Ser37 and found no change of phosphorylation at these sites (FIG. 1D), indicating that IMiDs selectively inhibit p53 phosphorylation at Ser15.

TABLE 5

| Genes | | Genes | |
|---|---|---|---|
| RRM1 | ↓* | KRAS | ↑* |
| RRM2 | ↓* | CDC25B | ↑ |
| FGFR3 | ↓ | CTSL2 | ↑ |
| MYC | ↓ | LAPTM5 | ↑ |
| JUND | ↓ | STAT3 | ↑ |
| TEAD3 | ↓ | RAD21 | ↑ |
| CCNE2 | ↓ | XPC | ↑ |
| CCNA1 | ↓ | SEC61A1 | ↑* |
| CCNA2 | ↓ | HLA-C | ↑ |
| CCNG1 | ↓ | ITM2B | ↑* |
| DLEC1 | ↓ | UBC | ↑* |
| MSX1 | ↓ | SMC4 | ↑ |
| MYBL2 | ↓* | RHOH | ↑* |
| ILR6 | ↓ | DDX3X | ↑* |
| CCR5 | ↓ | | |
| RAD51C | ↓ | | |
| CDKN3 | ↓ | | |
| DDX11 | ↓ | | |
| ZNF330 | ↓ | | |
| BID | ↓ | | |
| MKI67 | ↓ | | |
| CUL1 | ↓ | | |
| MAP2K6 | ↓* | | |

*p < 0.05

Previous studies have shown that Thalidomide (Thal), Len and Pom bind to an E3 ubiquitin ligase cereblon (CRBN), thereby facilitating proteasomal degradation of IKZF1/3, followed by downregulation of interferon regulatory factor 4 (IRF4). A recent study also defines other CRBN binding proteins in MM; however, to date there is no direct evidence that CRBN/IKZF/IRF4 axis directly modulates p53 activity. We here hypothesized that IMiDs may directly bind and modulate p53 or its related proteins, independent of CRBN.

Figure 7:
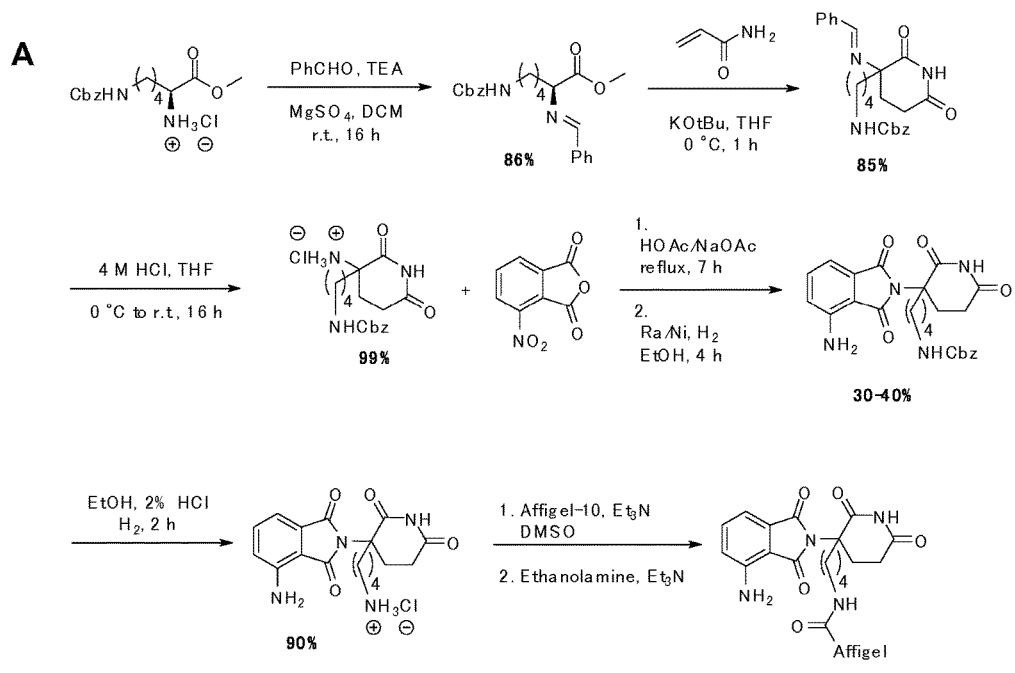
FIGS. 7A-B shows the synthetic scheme for preparing POM-immobilized beads (A) (adapted from PCT/US2006/002503, WO2006/081251A2), and the structures of Thal- and Len-immobilized beads and an FG bead-thallomide analog (B).
Figure 7:
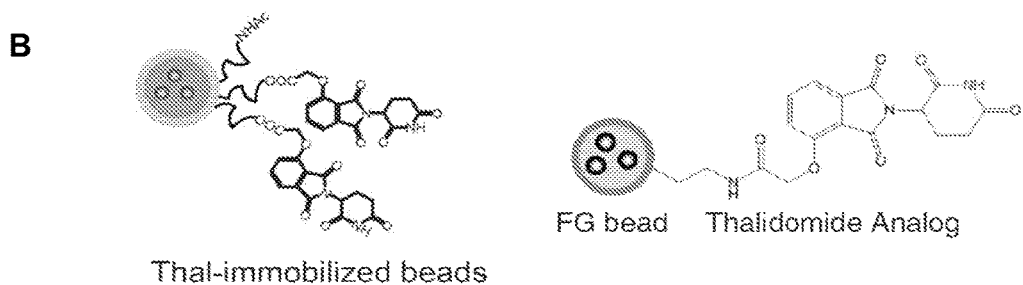
Figure 8:
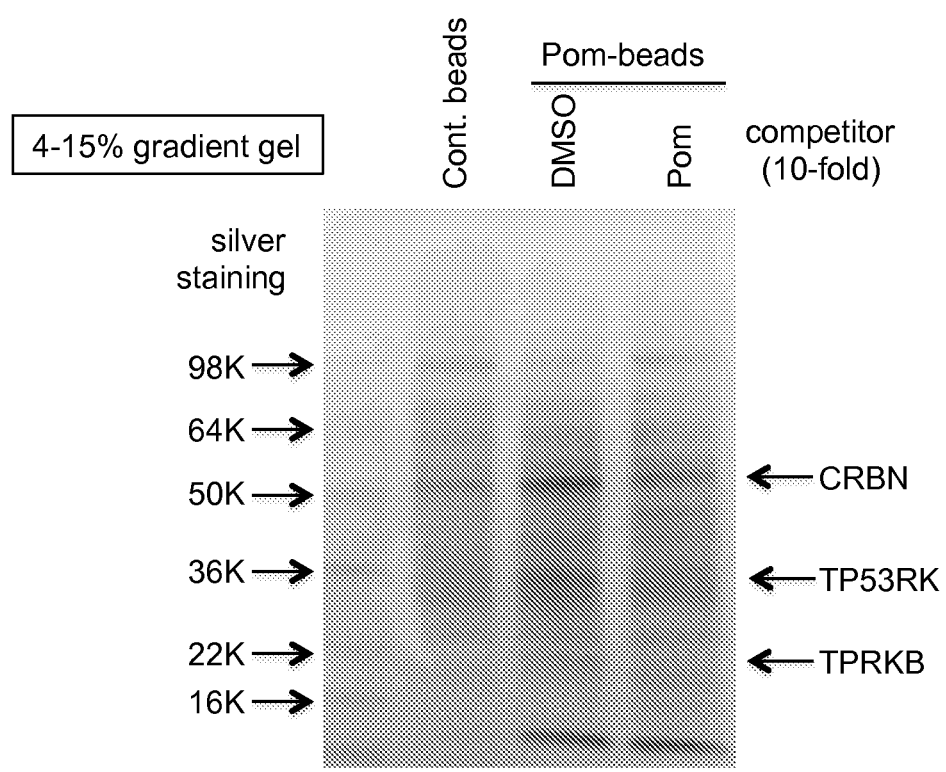
FIG. 8 is a photomicrograph of gel of the eluate of MM.1S whole cell lysates after incubation with POM-beads in the presence of absence of competitor.
Figure 9:
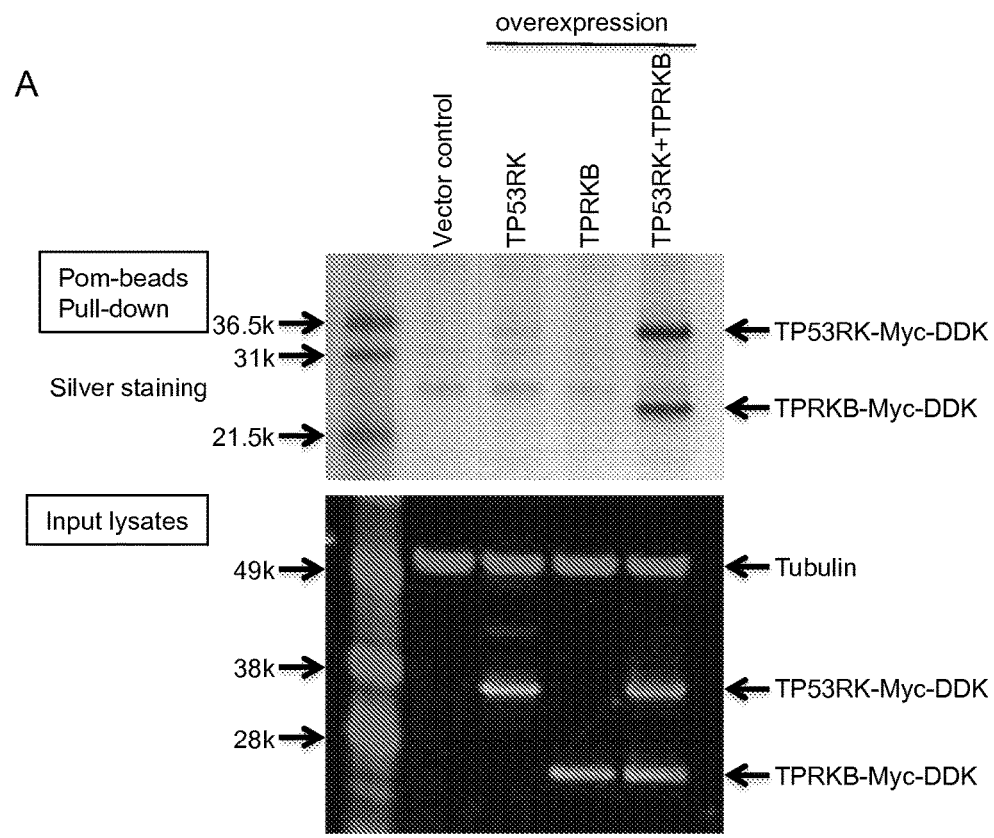
FIGS. 9A-B show gels (A) and Western blots (B) of eluates of whole cell lysates after incubation with POM beads in a pull-down assay.
Figure 9:
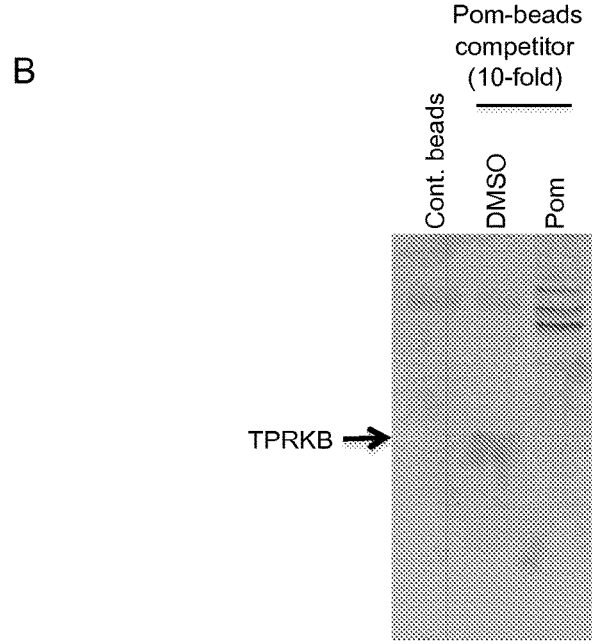

Since Pom has the most potent anti-MM activity among these IMiDs, we first generated Pom-immobilized beads (Pom-beads) (FIG. 1E and FIG. 7A), which are distinct from either Thal or Len-immobilized beads (FIG. 7B), for use in pull-down experiments. Of note, these Pom-beads maintained a MM growth inhibitory effect (data not shown). Importantly, CRBN, p53-related protein kinase (TP53RK, also known as PRPK) and its binding partner TP53RK binding protein (TPRKB), were pulled-down by Pom-beads, assessed by mass spectrometry (MS) (FIG. 8) and further confirmed by immunoblotting (FIG. 1F). In contrast, Thal-beads pulled down CRBN, as in previous studies, but did not pull down TP53RK. Although Pom-beads did not bind to either TP53RK or TPRKB alone, they bound when both proteins were co-overexpressed in HEK293F cells, indicating binding to TP53RK-TPRKB complex (FIG. 9A). Indeed, recombinant C-terminal Myc-DDK tagged TP53RK was also pulled down by Pom-beads (FIG. 9B).

Importantly, Pom in a dose-dependent fashion also markedly downregulated in vitro auto-phosphorylation of TP53RK (FIG. 1H), indicating that Pom directly binds and inhibits TP53RK. We further showed that Pom, but not Thal, induced downregulation of TP53RK and markedly reduced downstream p-p53 (FIG. 1I-J). Our results therefore for the first time show that Pom directly binds and inhibits TP53RK, thereby inhibiting p53 activity.

Figure 2:
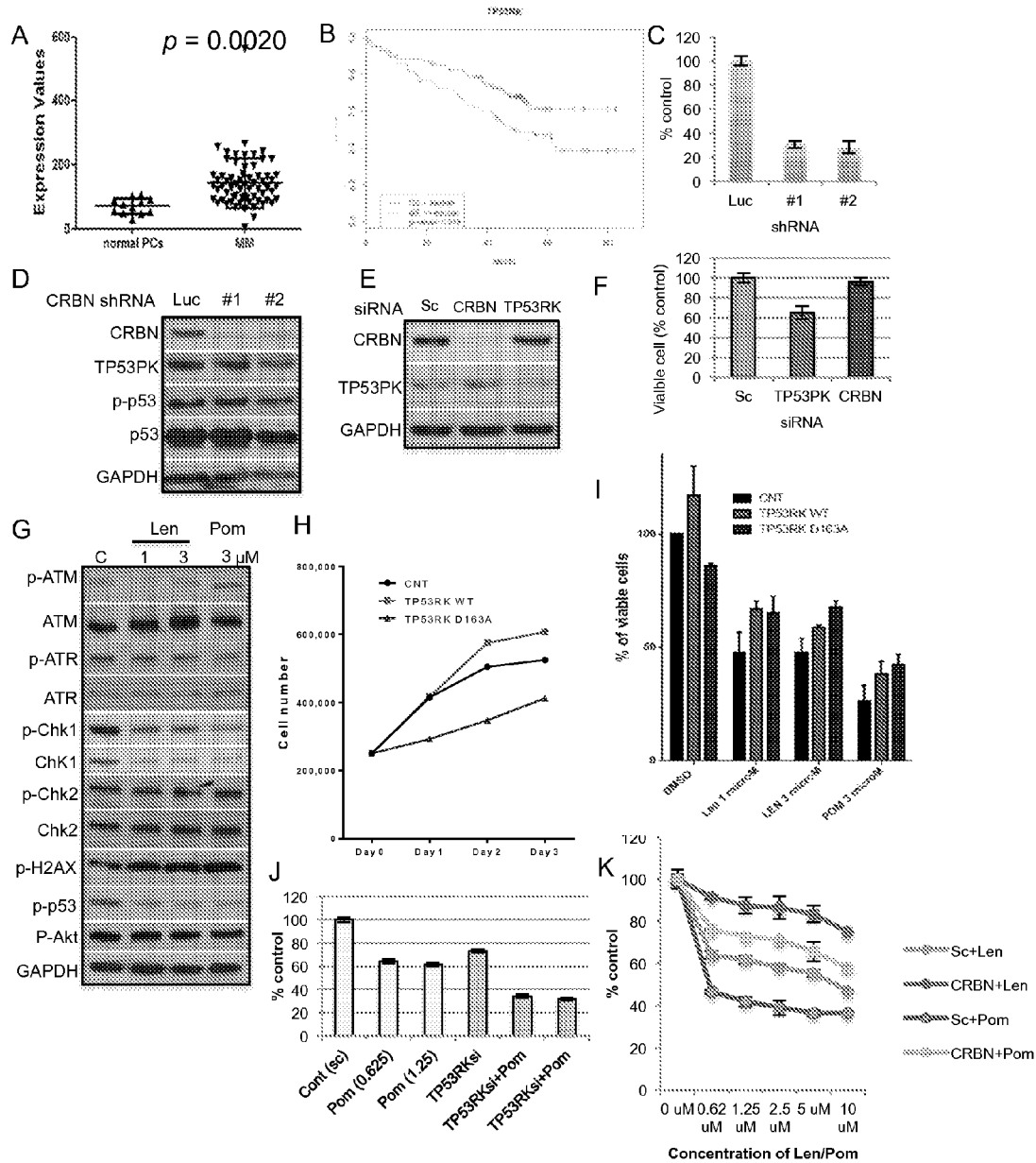
FIGS. 2A-K demonstrate the biological significance of TP53RK in MM.

Example 3. High TP53RK Expression in Newly Diagnosed Multiple Myeloma Patients Correlates with Shortened Survival Times We next examined the biologic and clinical significance of TP53RK in MM cells. Gene expression profiling (GEP) shows that MM cells express higher levels of TP53RK than normal plasma cells (FIG. 2A) or plasma cells from monoclonal gammopathy of undetermined significance (MGUS) and smoldering MM (SMM) (FIG. S10A), suggesting that TP53RK expression correlates with progression of MM. Moreover, newly diagnosed patients with MM expressing high TP53RK have significantly shorter survival than those with whose tumor cells express low levels of TP53RK ($p=0.018$) (FIG. 2B).

Example 4. Pom Binds and Regulates TP53RK and CRBN Via Independent Mechanisms

Figure 10:
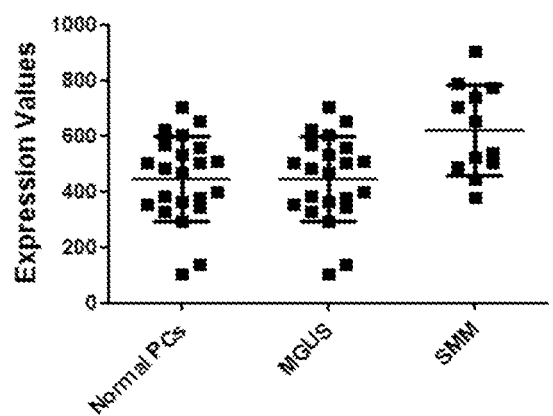
FIGS. 10A-B shows a graph (A) of comparative gene expression profiling analysis between normal plasma cells (PCs), monoclonal gammopathy of undetermined significance (MGUS), and smoldering MM (SMM); and a Western blot (B) of whole cell lysates from MM cell lines.
Figure 10:
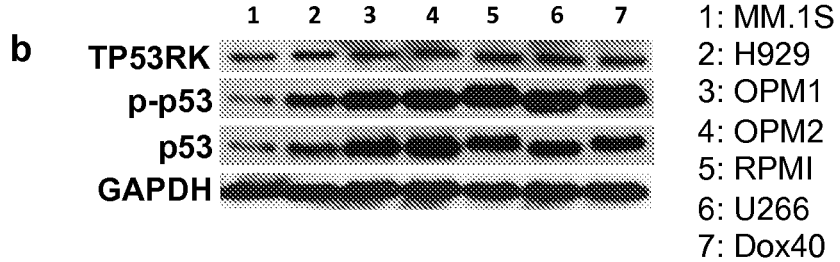
Figure 11:
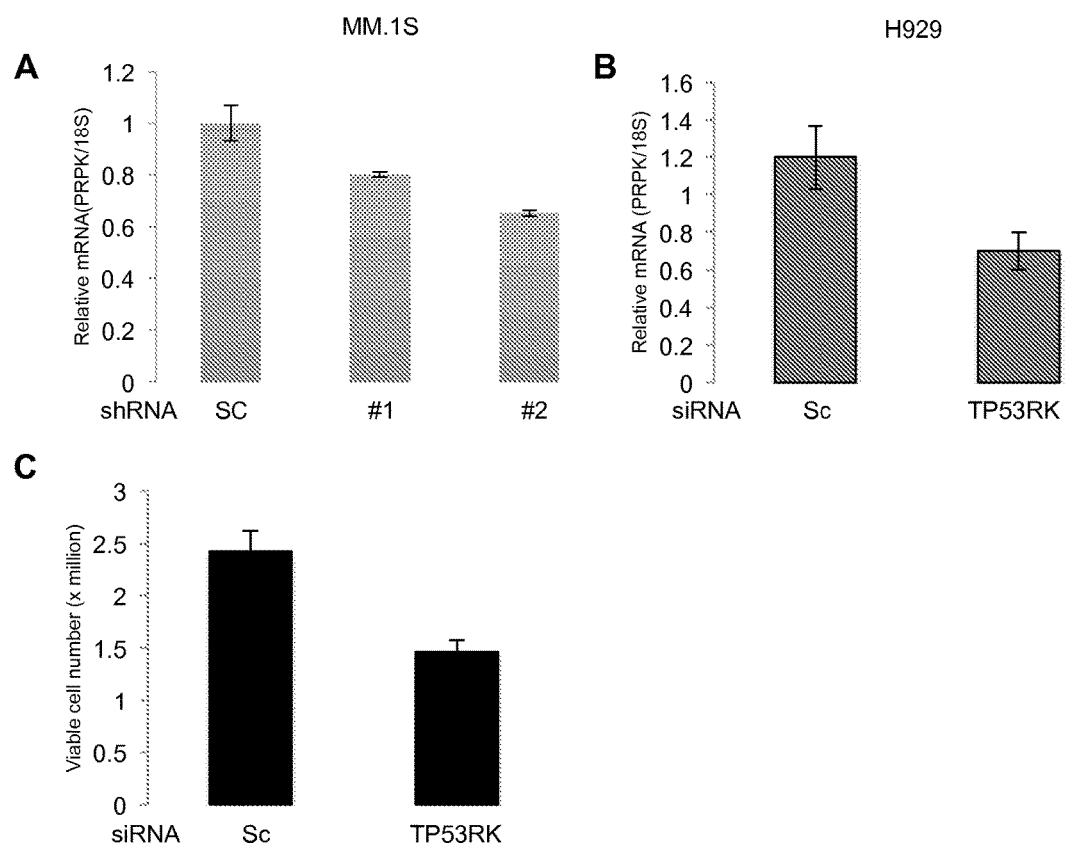
FIGS. 11A-C show histograms of the relative mRNA levels of TP53RK in MM.1S cells (A) and H929 cells (B) were transfected with scrambled or TP53RK siRNA, and viable cell number (C).

TP53RK is constitutively expressed in MM cell lines, regardless of p53 status (FIG. 10B). Since TP53RK is highly expressed in patient MM cells and MM cell lines, we next used shRNA and siRNA to evaluate sequelae of TP53RK knock-down in MM.1S and H929 cells: mRNA levels were markedly decreased (FIG. 11A-B), associated with growth inhibition in both MM.1S (FIG. 2C) and H929 cells (FIG. 11C). Since previous studies have shown that CRBN is the only direct binding protein of IMiDs, we next determined whether CRBN modulates TP53RK protein expression and/or function. CRBN knock-down did not alter TP53RK, p53 or p-p53 expression in MM.1S cells (FIG. 2D); and conversely, TP53RK downregulation did not modulate CRBN expression in H929 cells (FIG. 2E). TP53RK, but not CRBN, knock-down triggered MM cell growth inhibition (FIG. 2F). Moreover, Thal-beads pulled-down CRBN, but not TP53RK (FIG. 1G). Taken together, these results indicate that Pom binds and regulates TP53RK and CRBN in independent mechanisms.

Example 5. p-53 Downregulation Triggered by IMiDs is Independent of DNA Damage-Mediated Signaling Pathways DNA damage triggers phosphorylation of p53 at different serine residues: activated ATM, ATR or DNA-PK phosphorylate Ser15 and/or Ser37; whereas Chk1/2 phosphorylates Ser20. Since MM cells have ongoing constitutive DNA damage, we next asked whether IMiDs directly downregulate serine residues of p53 by inhibiting these kinases.

Len or Pom treatment inhibited phosphorylation of Chk1, but not ATM, ATR or Chk2 (FIG. 2G). Coupled with a lack of p-Ser20 modulation (FIG. 1D), these results suggest that p-53 downregulation triggered by IMiDs is independent of a DNA damage-mediated signaling pathway.

Figure 12:
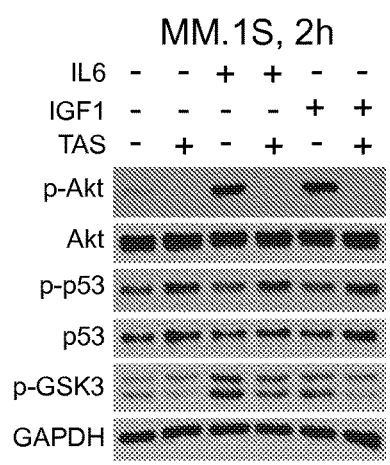
FIG. 12 is a Western blot of whole cell lysates of MM1.S cells cultured with IL-6 or IGF1 in the presence or absence of the Akt inhibitor TAS-117.

Example 6. Phosphorylation and Activity of TP53RK in MM Cells is not Mediated by Akt TP53RK can be phosphorylated at Ser250 by Akt, and so we next determined whether downregulation of TP53RK phosphorylation triggered by Pom is mediated, at least in part, via Akt inhibition. MM.1S cells were treated with Akr inhibitor TAS-116 or cytokines (IL-6, IGF1) to inhibit or activate Akt, respectively; in neither case was p-p53 modulation observed, (FIG. 12), indicating that phosphorylation and activity of TP53RK in MM cells is not mediated by Akt.

Figure 13:
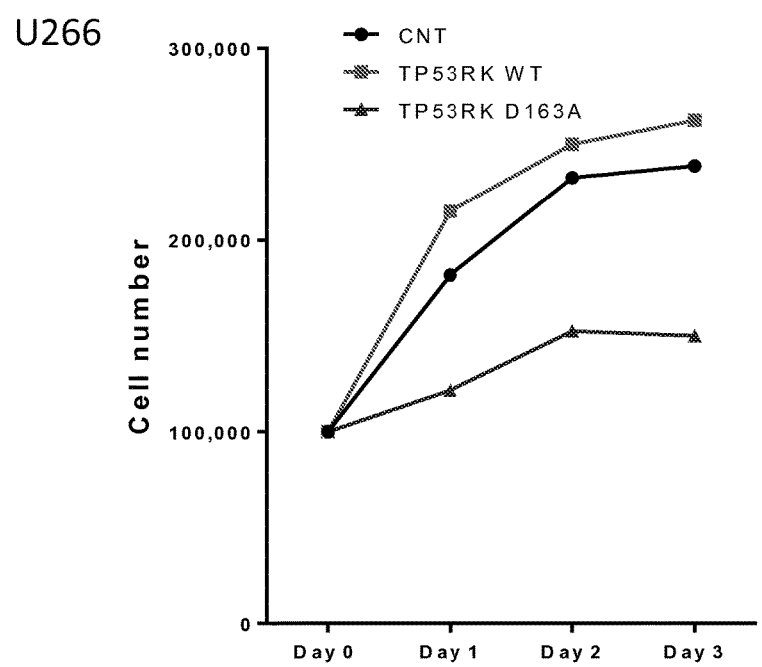
FIG. 13 is a graph showing viable cell number in U266 cells transfected with either scambled (CNT), wt- or kinase-dead (D163A)-TP53RK.

Example 7. TP53RK Plays a Crucial Role in Cell Growth and Mediating Effects of IMiD Treatment in MM Cells We next examined the effect of wild-type (wt) and kinase-dead mutant (D163A) TP53RK, alone and in combination with Len or Pom, on MM cell growth. Wt-TP53RK enhanced, whereas mutant TP53RK decreased, growth of H929 cells (FIG. 2H) and U266 cells (FIG. 13). In addition, D163A, but not wt, TP53RK abrogated growth inhibition triggered by Len or Pom (FIG. 2I). Moreover, TP53RK knockdown significantly ($p<0.02$) enhanced Pom-induced MM cell growth inhibition in H929 cells (FIG. 2J). Although previous studies show that downregulation of CRBN completely abrogates IMiDs-induced cytotoxicity, our results indicate that CRBN knock-down only partially abrogates cell death triggered by Len or Pom (FIG. 2K), associated with differences in p53 status of cells studied, ie OPM2 cells (mutant p53) and H929 cells (wt-p53). Our results therefore show that TP53RK plays a crucial role in cell growth and mediating sequelae of IMiDs treatment in MM cells.

Example 8. iMIDs Trigger p53-Mediated Autophagy

Figure 14:
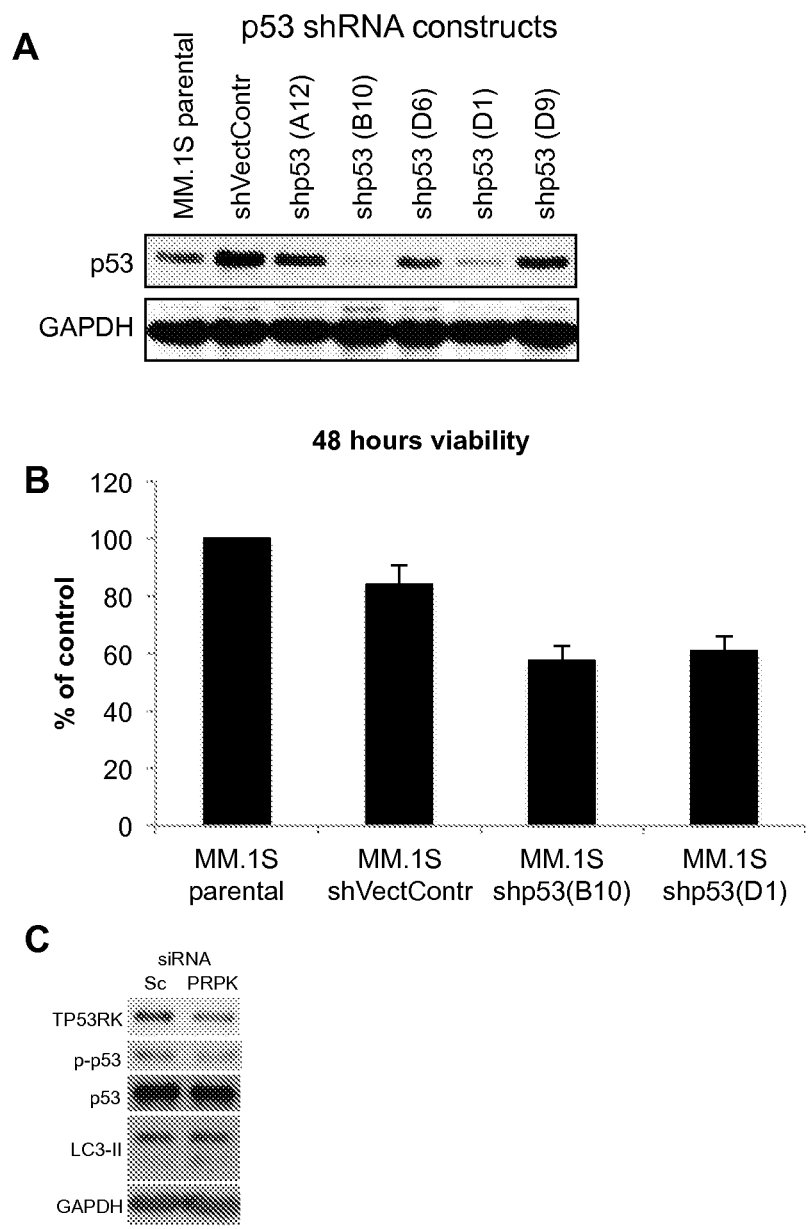
FIGS. 14A-C are Western blots (A and C) of MM.1S and H929 whole cell lysates; and a histogram (B) of MM.1S cell viability over 48 hours.

We next examined the biologic significance of p53 inhibition in MM cells using genetic knockdown and pharmacological inhibition strategies. Lentiviral p53 shRNA decreased both p53 and cell growth in MM.1S cells (FIG. 3A and FIG. 14A). Previous studies have demonstrated growth inhibition in p53 deficient cells via induction of autophagy with upregulated LC3-II; and we here showed that LC3-II increased in MM.1S and H929 cells after p53 knockdown (FIG. 3A), indicating that p53 downregulation induces autophagy in MM cells. Similar results were observed in H929 cells after TP53RK siRNA knockdown, further confirming that TP53RK-p53 axis mediates autophagic death in MM cells (FIG. 14B). Pharmacological inhibition of TP53RK by IMiDs similarly upregulated LC3-II and pro-apoptotic Bim (FIG. 3B).

Since TP53RK is essential for regulation of rapamycin (TOR) and its downstream targets and mTOR in turn plays a crucial role in autophagic cell death, we also examined whether TP53RK knockdown or IMiDs inhibit phosphorylation of S6K due to mTOR inhibition: no inhibition of p-p70S6K was noted in either case (data not shown). To further confirm the role of p53-mediated autophagy in IMiDs treatment, we cultured MM.1S cells with IMiDs, in the presence or absence of MDM2 inhibitor Nutlin-3a (Nut3). Nut3 upregulated p-p53 and p53 by protecting against proteasomal degradation, which was inhibited by Len or Pom. Moreover, upregulation of LC3-II triggered by Len and Pom was markedly downregulated by Nut3 (FIG. 3C), further confirming the p53-mediated autophagy triggered by IMiDs.

Figure 15:
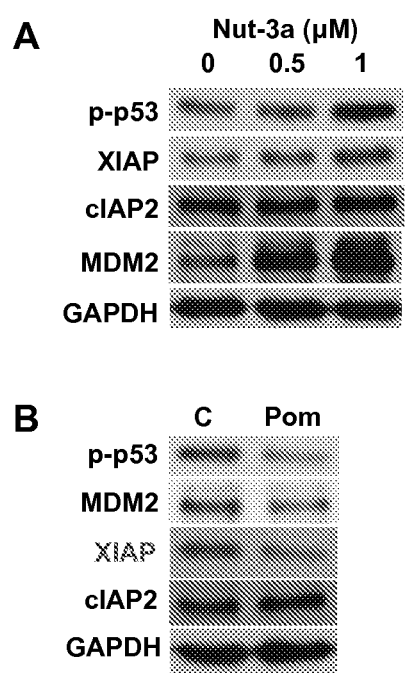
FIGS. 15A-B are Western blots of whole cell lysates of MM.1S cells cultured with nutlin-3a (Nut-3) (A) or Pom (B) for 48 hours.

Example 9. IMiD-Induced Cytotoxicity in Multiple Myeloma is Mediated Via Apoptosis Through Inhibition of the TP53RK-p53-E2F-Bim Axis and Autophagy, Independent of mTOR Inhibition IMIiDs also triggered PARP cleavage, which was enhanced by Nut3 (FIG. 3C), and we therefore next delineated mechanisms of apoptosis. Previous studies have shown transcriptional regulation of MDM2 by p53, as well as modulation of X-linked inhibitor of apoptosis protein (XIAP) by MDM2. Since XIAP is a potent anti-apoptotic protein in MM, we determined whether p53 knockdown and/or IMiDs treatment inhibit XIAP expression via MDM2 downregulation. Indeed, p53 knockdown by shRNA downregulated both MDM2 and XIAP in MM.1S cells (FIG. 3D); conversely, MDM2 inhibitor Nut3 upregulated their expression (FIG. 15A). IMiDs similarly downregulated MDM2, associated with decreased expression of cIAP, but not cIAP2 (FIG. 3E and FIG. 15B).

Figure 3:
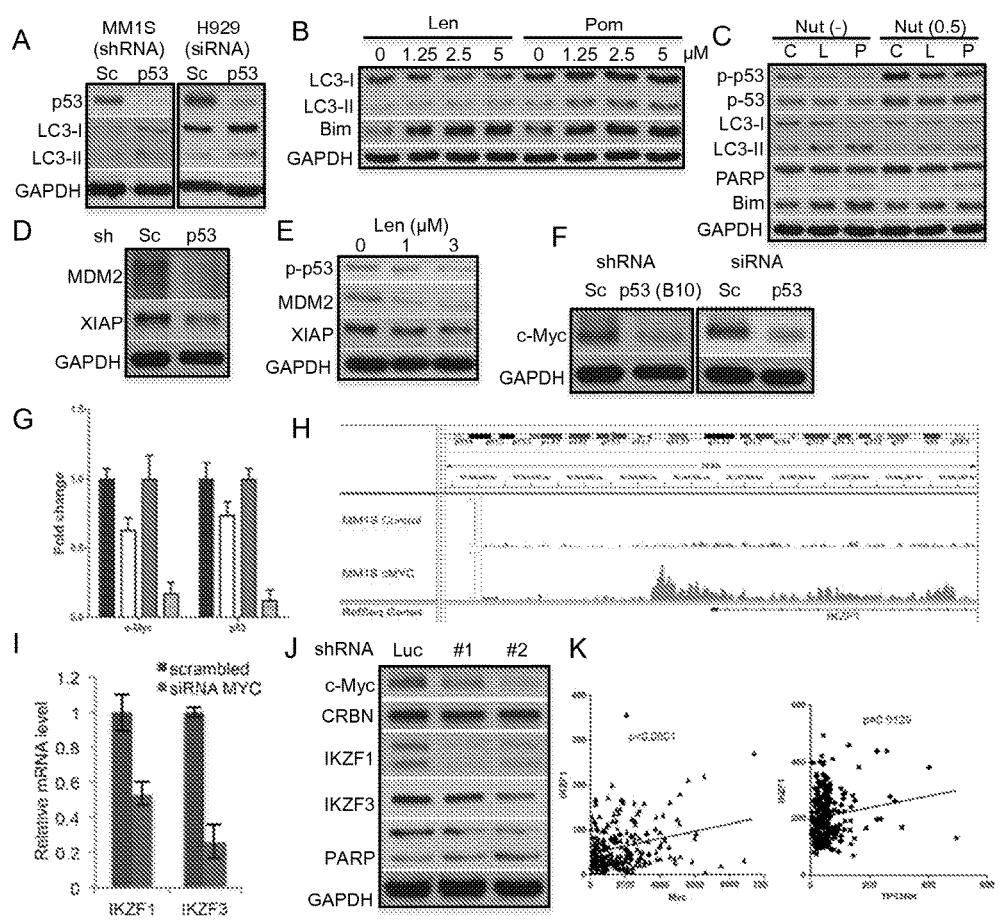
FIGS. 3A-K demonstrate that p53 inhibition triggers MM cell growth inhibition.
Figure 16:
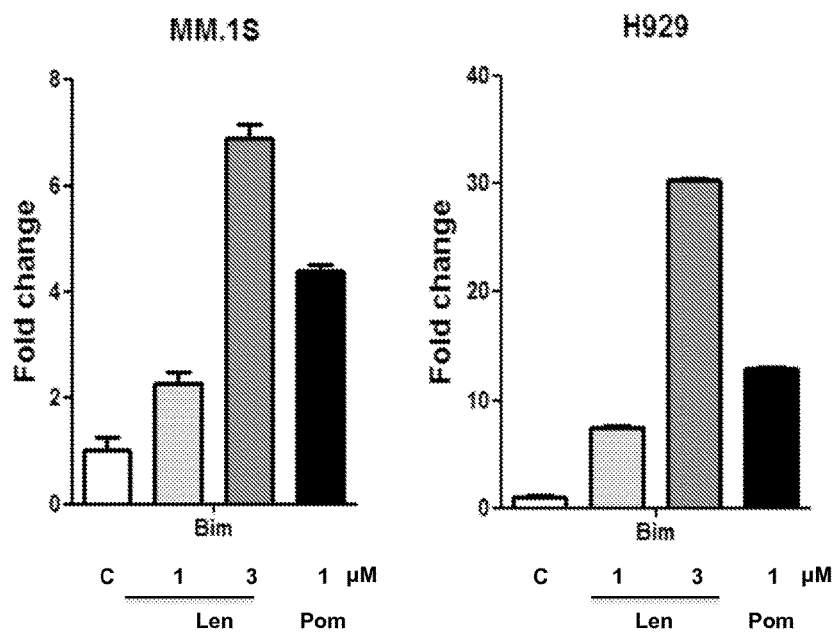
FIG. 16A is a histogram showing the fold change of Bim in MM.1S and H929 cells treated with Len or Pom.
FIGS. 16B and C show the results of electrophoretic mobility shift assays (EMSA) used to assess E2F1 DNA binding activity at varying concentrations of Len or Pom.
Figure 16:
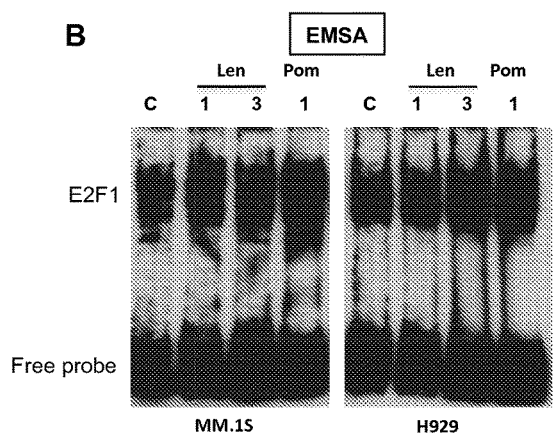
Figure 16:
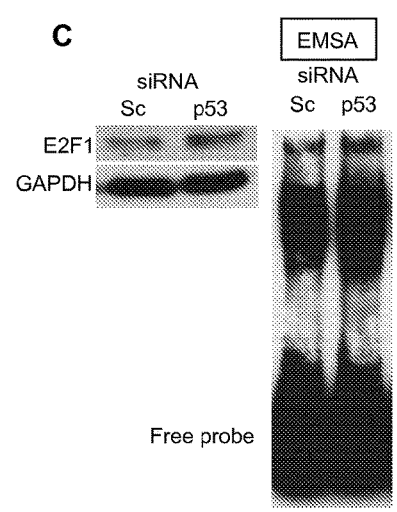
Figure 17:
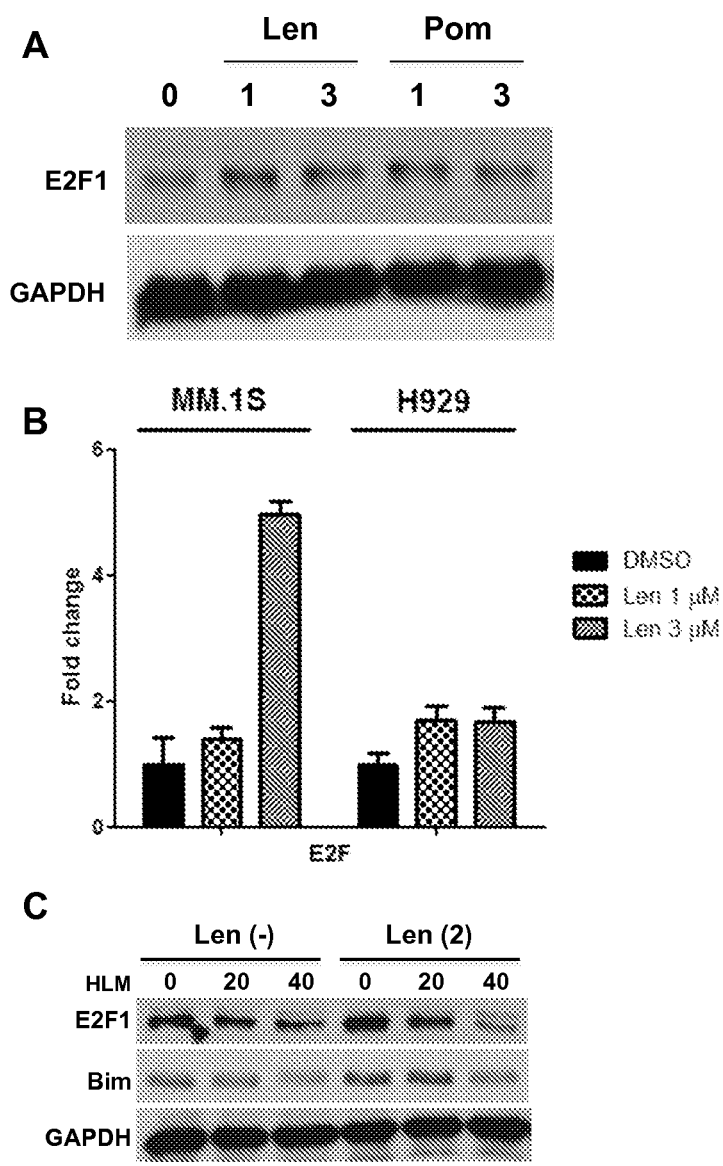
FIGS. 17A-C show Western blots (A and C) and a histogram (B) from experiments demonstrating that Len and Pom increase E2F protein and mRNA levels in MM.1S and H929 cell lines.

Importantly, we also observed upregulation of pro-apoptotic protein Bim in IMiDs-treated cells (FIG. 3B-C). Real-time qPCR showed that upregulation of Bim triggered by IMiDs was due to enhanced transcription (FIG. 16A). Bim is transcriptionally regulated by E2F, and we here show that IMiDs enhance DNA binding activity of E2F1, confirmed by EMSA (FIG. 16B). Furthermore, p53 knockdown upregulated E2F1 DNA binding activity (FIG. 16C), indicating that IMiDs-induced E2F1 activation and Bim upregulation are due to p53 inhibition. Finally, IMiDs treatment increased levels of both E2F1 protein (FIG. 17A) and mRNA (FIG. 17B). Enhanced E2F1 DNA binding activity may therefore be due to increased E2F1 protein levels; conversely, E2F inhibitor HLM006474 blocked IMiDs-induced Bim upregulation in a dose-dependent fashion (FIG. 17C), suggesting that IMiDs induced upregulation of Bim is mediated via E2F1 activation. These results indicate that IMiDs-induced cytotoxicity in MM is mediated via apoptosis through inhibition of TP53RK-p53-E2F-Bim axis and autophagy.

Figure 18:
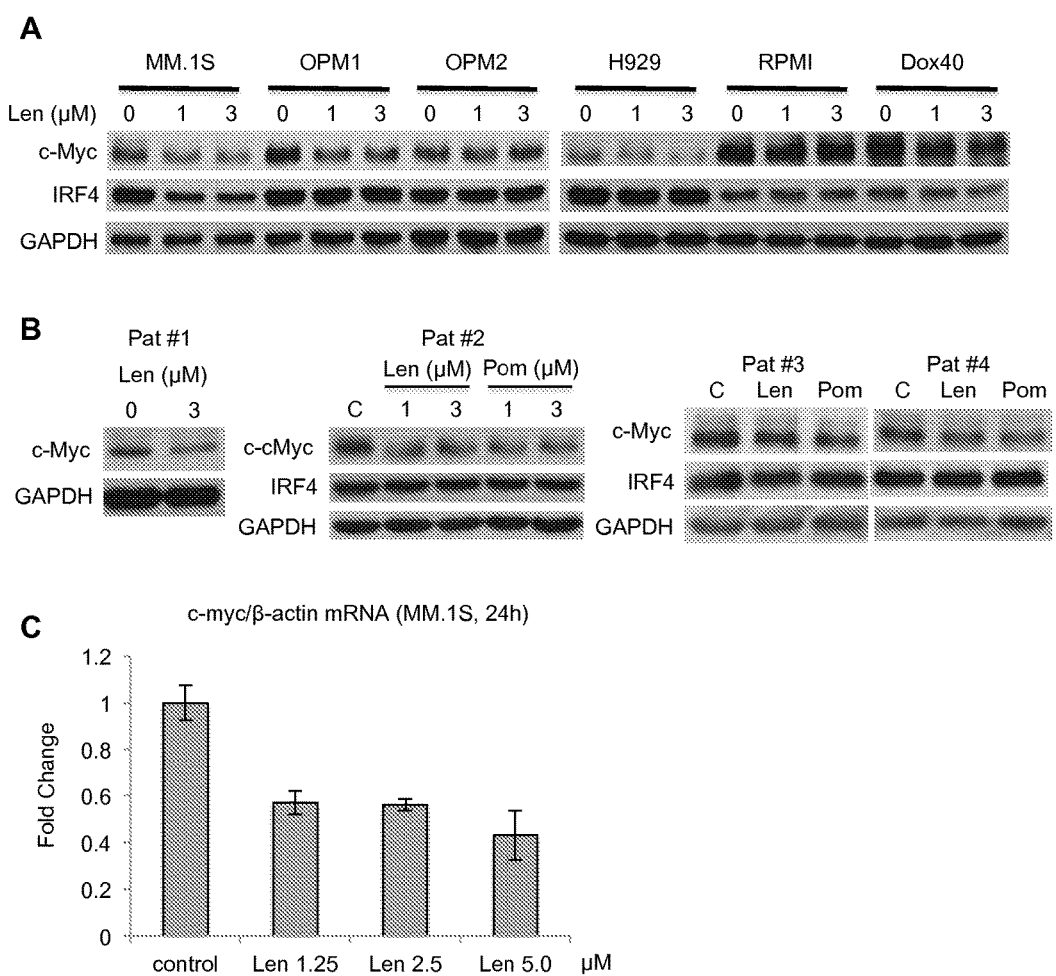
FIGS. 18A-C show Western blot analysis of IMiDs-sensitive cell lines (A) and MM patient cells (B) for the effect of IMiDs on c-Myc. The histogram (C) shows real-time PCR results of m RNA extracted from MM.1S cells treated with increasing concentrations of Len.
Figure 19:
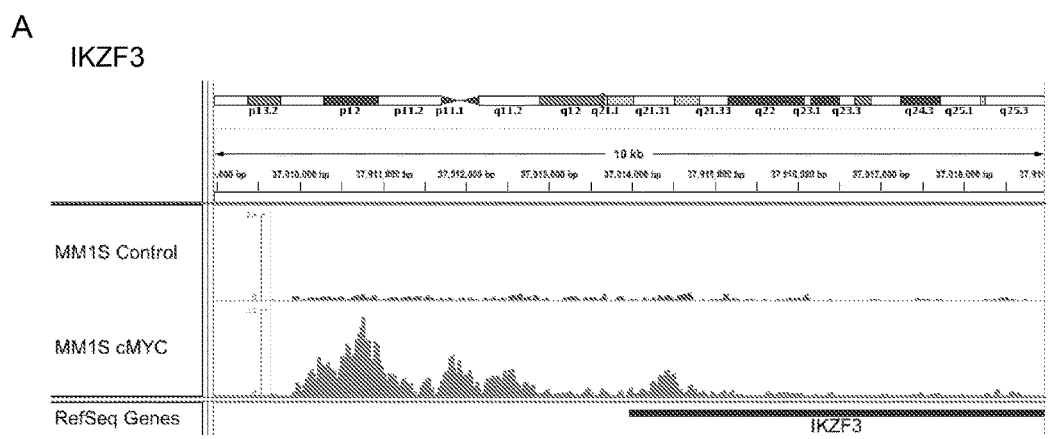
FIGS. 19A-C show the results from experiments performed in H929 cells to determine whether TP53RK knockdown modulates the CRBN.IKZF axis via the p53-c-Myc axis.
Figure 19:
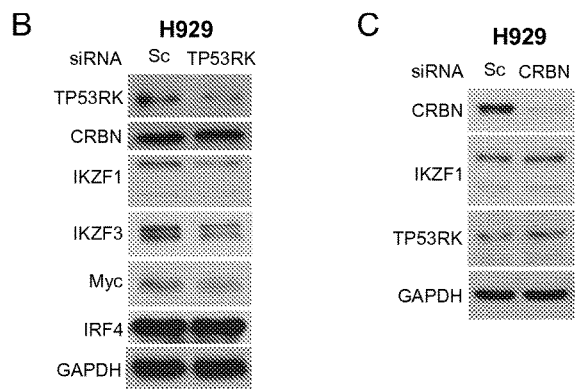

Example 10. TP53RK Mediates Downregulation of c-Myc c-Myc plays a crucial role in MM pathogenesis. We unexpectedly observed c-Myc protein (FIG. 3F) and mRNA (FIG. 3G, left panel) downregulation after p53 knockdown; and conversely, that c-Myc knockdown downregulated p53 mRNA (FIG. 3G, right panel), suggesting cross-talk between p53 and c-Myc. IMiDs bind to CRBN, facilitating proteasomal degradation of IKZF1/3. Importantly, IMiDs downregulate c-Myc in IMiDs sensitive (MM.1S, H929, OPM1) cell lines (FIG. 18A) and patient MM cells (FIG. 18B). Real-time qPCR confirms that downregulation of c-Myc triggered by Len or Pom is due to decreased transcription (FIG. 18C). Importantly, by analyzing previously reported ChIP-sequence data we delineated c-Myc binding to promoter regions in both IKZF1 (FIG. 3H) and IKZF3 (FIG. 19). Regulation of IKZF1/3 by c-Myc was further confirmed in c-Myc knockdown MM cells using qPCR (FIG. 3I). We therefore next determined whether TP53RK knockdown modulates CRBN/IKZF axis via p53-c-Myc axis. Although CRBN expression was not altered by TP53RK knockdown, IKZF1/3 were markedly downregulated in both MM.1S cells (FIG. 3J) and H929 cells (FIG. 19B). Moreover, CRBN knockdown did not change TP53RK expression, indicating that expression of these proteins is regulated independently (FIG. 19C). Indeed our analysis of GEP data showed that TP53RK, c-Myc, and IKZF1 expression were significantly correlated in patient MM cells (FIG. 3K). Taken together, these results indicate that downregulation of c-Myc by IMiDs is mediated not only by IRF4, but also by the TP53RK-p53 pathway; and demonstrate a regulatory loop between p53 and c-Myc in MM cells. IMiDs therefore regulate IKZF1/3 expression via two mechanisms: CRBN-IRF4 axis via their proteasomal degradation; as well as TP53RK-p53-c-Mycaxis via transcriptional regulation.

Figure 4:
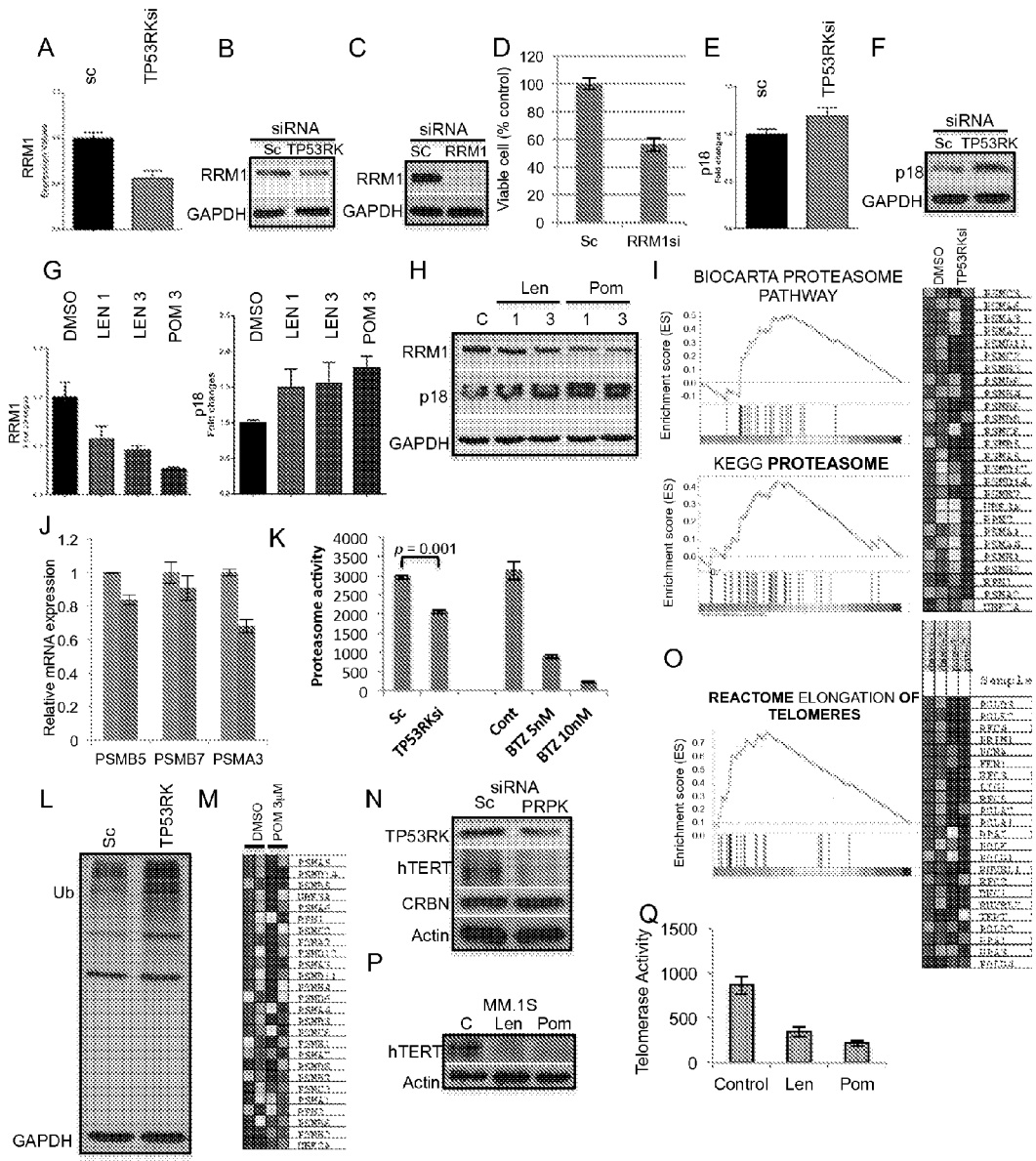
Figure 5:
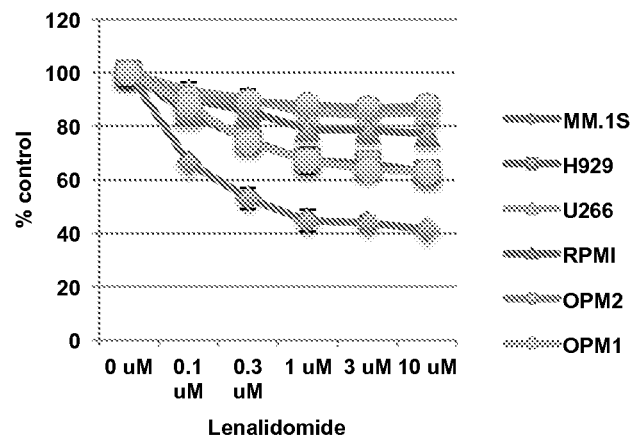
FIGS. 5A-B are graphs showing the sensitivity of various cells lines having either wild type or mutant p53 to Len (A) and Pom (B).
Figure 5:
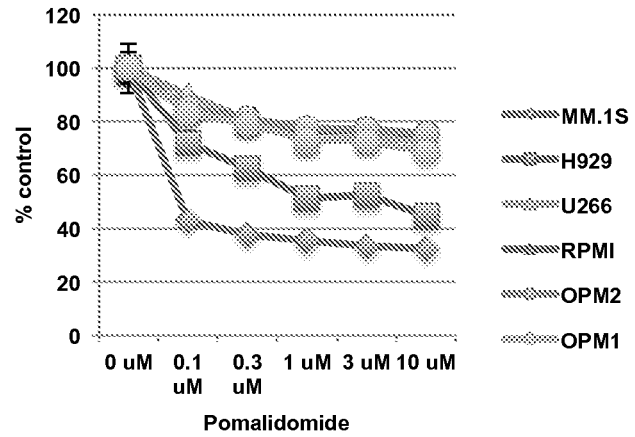

Example 11. TP53RK Regulates RRM1 and CDK4/6 in Multiple Myeloma Cells p53 is thought to be the only downstream target of TP53RK. To determine whether TP53RK regulates additional molecules or pathways, we carried out gene expression profiling analyses (GSEA) and validation before and after TP53RK knock down in H929 cells. In these analyses, we identified genes downregulated (Table 6) or upregulated (Table 7) by TP53RK knockdown. We next validated MM relevant genes including ribonucleotide reductase (RRM1) and CDK4/6 inhibitor p18CDKN2C. RT-qPCR (FIG. 4A) and Western blot (FIG. 4B) showed downregulation of RRM1 by TP53RK knockdown. We confirmed that downregulation of RRM1 by siRNA (FIG. 4C) triggered significant MM cytotoxicity (FIG. 4D). We also confirmed upregulation of p18CDKN2C by RT-qPCR (FIG. 4E) and Western blot (FIG. 4F). Similar to TP53RK knockdown, Len and Pom also downregulate RRM1 and upregulate p18CDKN2C, evidenced by RT-qPCR (FIG. 4G) and Western blot (FIG. 4H). Previous studies have shown that p18CDKN2C is regulated by E2F1 and we here show that either Len/Pom or p53 knockdown increases E2F1 (FIG. 16A-C), suggesting that IMiD-induced upregulation of p18CDKN2C is mediated via the TP53-p53-E2F1 pathway in MM cells.

TABLE 6

Downregulated genes by TP53 knockdown

|   | Probe set | Gene name | Correlation to survival |
|---|---|---|---|
| 1 | 225402_at | TP53RK | YES |
| 2 | 224996_at | ASPH | NO |
| 3 | 1558747_at | SMCHD1 | YES |
| 4 | 227223_at | RBM39 | NO |
| 5 | 227804_at | TLCD1 | NO |
| 6 | 239002_at | ASPM | YES |
| 7 | 223555_at | GON4L | NO |
| 8 | 218349_s_at | ZWILCH | YES |
| 9 | 201476_s_at | RRM1 | NO |
| 10 | 1558093_s_at | MATR3 | NO |
| 11 | 241367_at | TEX19 | NO |
| 12 | 200950_at | ARPC1A | NO |
| 13 | 222713_s_at | FANCF | YES |
| 14 | 203974_at | HDHD1A | NO |
| 15 | 219953_s_at | AKIP1 | NO |
| 16 | 225383_at | ZNF275 | NO |
| 17 | 207983_s_at | STAG2 | NO |
| 18 | 208744_x_at | HSPH1 | NO |
| 19 | 227627_at | SGK3 | NO |

TABLE 7

Upregulated genes by TP53 knockdown

|   | Probe set | Gene name | Correlation to survival |
|---|---|---|---|
| 1 | 238761_at | ELK4 | NS |
| 2 | 236715_x_at | UACA | NS |
| 3 | 217559_at | RPL10L | NS |
| 4 | 230173_at | TRIM4 | YES |
| 5 | 219238_at | PIGV | YES |
| 6 | 232197_x_at | ARSB | YES |
| 7 | 214594_x_at | ATP8B1 | NS |

TABLE 7-continued

Upregulated genes by TP53 knockdown

| | Probe set | Gene name | Correlation to survival |
|---|---|---|---|
| 8 | 224681_at | GNA12 | NS |
| 9 | 215856_at | SIGLEC15 | YES (but negative) |
| 10 | 216169_x_at | ZC3H7B | YES |
| 11 | 214707_x_at | ALMS1 | NS |
| 12 | 208137_x_at | ZNF611 | NS |
| 13 | 1558290_a_at | PVT1 | NS |
| 14 | 233543_s_at | FAM175A | NS |
| 15 | 203110_at | PTK2B | NS |
| 16 | 232975_at | HCG18 | NS |
| 17 | 220232_at | SCD5 | YES |
| 18 | 205745_x_at | ADAM17 | NS |
| 19 | 1569409_x_at | INHBA | NS |

Example 12. Pom-Induced Proteasome Inhibition is Mediated Via TP53RK

Figure 20:
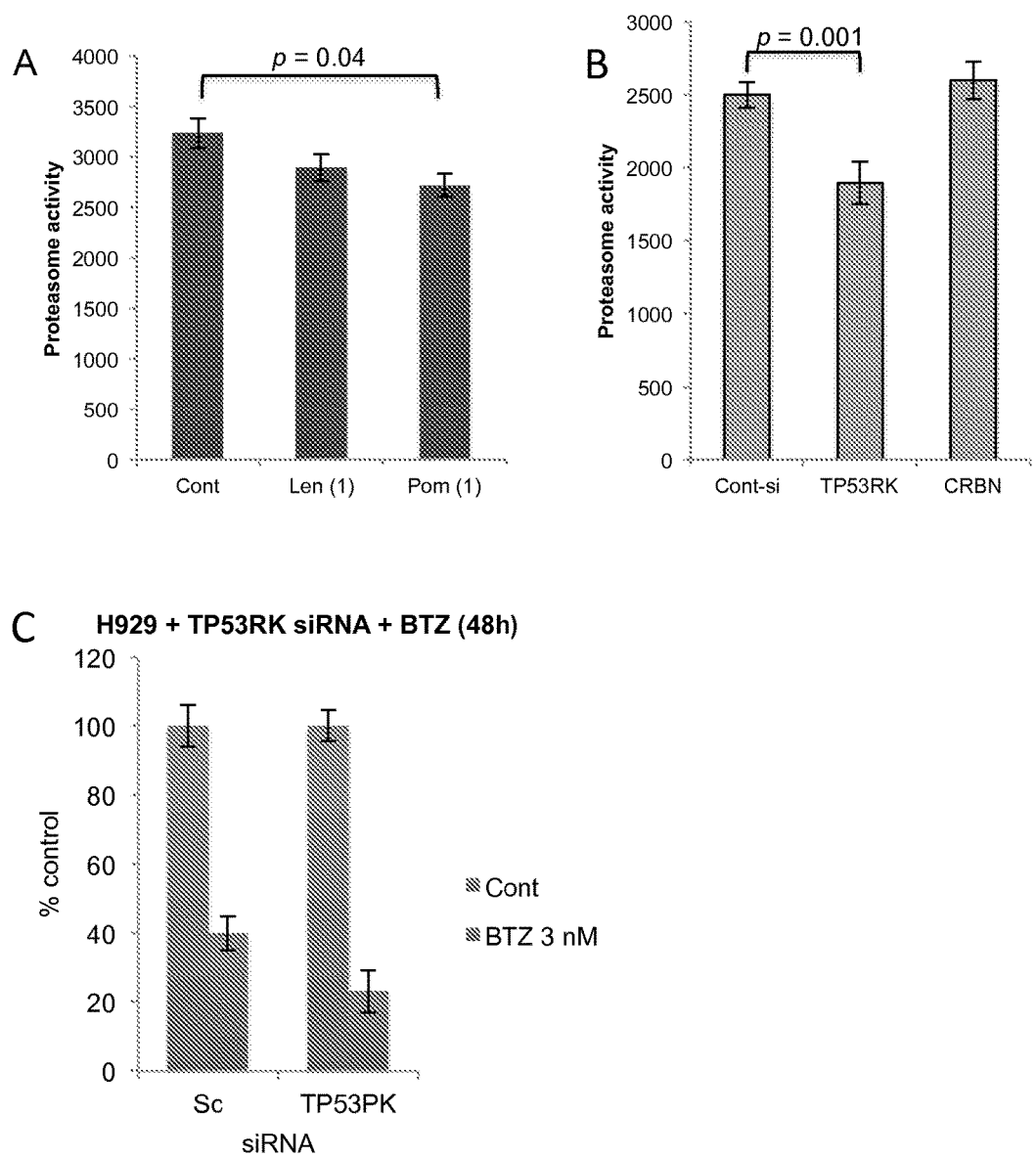
FIGS. 20A-C show the results of a study in H929 cells to determine the effect of IMiDs on proteasome activity.

GSEA also identified the proteasome pathway to be downregulated by TP53RK knockdown (FIG. 4I). RT-qPCT confirmed downregulation of PSMB5 PSMB7 and PSMA3 (FIG. 4J). In addition, chymotrypsin-like proteasome activity was significantly inhibited (FIG. 4K), resulting in accumulation of poly-ubiquitinated proteins (FIG. 4L). GSEA of Pom-treated cells also showed downregulation of proteasome pathway (FIG. 4M) and activity (FIG. 20A). TP53RK, but not CRBN, knockdown altered proteasome activity (FIG. 20B), indicating that Pom-induced proteasome inhibition is mediated via TP53RK. Of note, TP53RK knockdown further enhanced cytotoxicity induced by proteasome inhibitor bortezomib (BTZ) (FIG. 20C).

Figure 21:
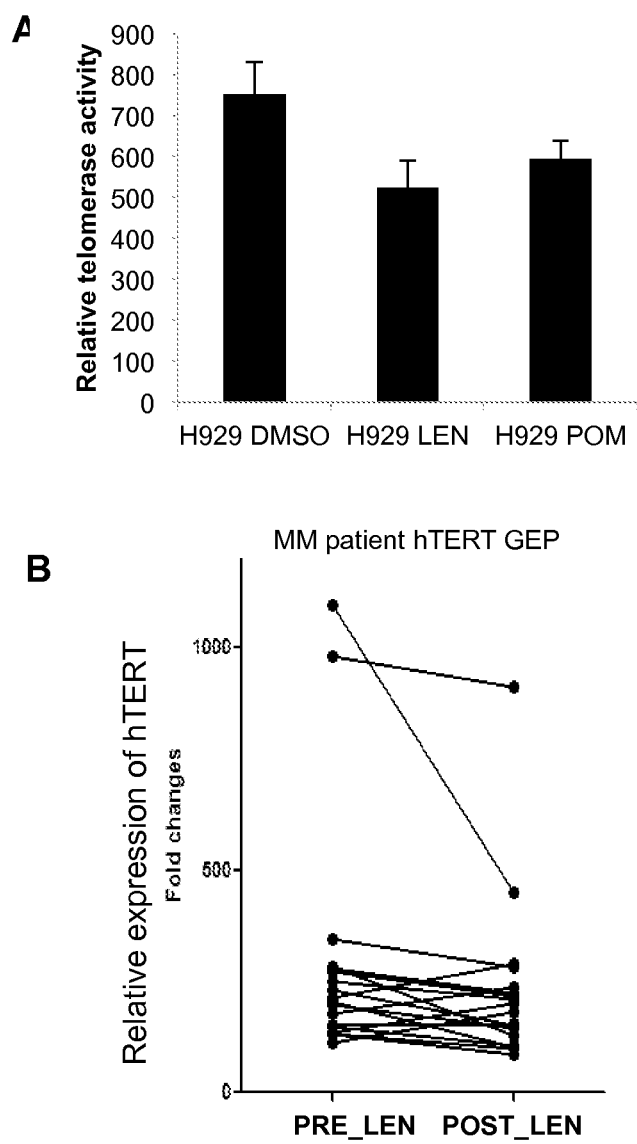
FIGS. 21A-B show the results from experiments performed in H929 cells treated with IMiDs to determine their effect on hTERT expression.

Example 13. Len and Pom Treatment Inhibit hTERT Expression in Multiple Myeloma Cells Previous studies have demonstrated that the "kinase, endopeptidase and other proteins of small size (KEOPS)" complex promotes telomere uncapping and elongation. Since TP53RK is part of the KEOPS complex, we next determined whether TP53RK knockdown affects expression and/or activity of telomerase reverse transcriptase (TERT). TP53RK knockdown downregulated hTERT expression in H929 cells (FIG. 4N). Moreover, both Len and Pom treatment of MM.1S cells and H929 cells significantly inhibited hTERT expression (FIG. 4P) and activity (FIG. 4Q) (FIG. 21A). Importantly, GEP analysis of MM patient samples showed lower hTERT levels after Len treatment (FIG. 21B), indicating that IMiDs may impair telomere maintenance by inhibiting TP53RK.

FIG. 22 shows a suggested mechanism of action in which Pom and/or TP53RK inhibition trigger anti-MM activity. Pom binds CRBN and triggers proteasomal degradation of IKZF1/3, followed by IRF4 inhibition. Pom also binds the TP53RK-TPRKB complex and inhibits TP53RK activity, thereby inhibiting p53 activity. Inhibition of p53 activity: (1) decreases MDM2 and downstream XIAP expression, as well as activates E2F-dependent Bim expression, leading to both apoptotic and autophagic MM cell death; and (2) downregulates c-Myc and its target IKZF1/3. IKZF1/3 expression after IMiDs treatment is therefore regulated by CRBN and related proteasomal degradation, as well as transcriptional inhibition of c-Myc via the PRPK-p53 axis. Inhibition of TP53RK also induces (3) downregulation of RRM1 and hTERT, as well as upregulation of p18CDKN2C expression.

It is to be understood that the foregoing description is intended to illustrate and not to limit the scope of the invention, which is defined by the scope of the appended claims. Other embodiments are within the scope of the following claims.

What is claimed is:

1. A method of inhibiting proliferation or migration of a multiple myeloma cell, the method comprising administering to a subject in need thereof a TP53RK antagonist in an amount effective to inhibit proliferation or migration of the multiple myeloma cell,
wherein the TP53RK antagonist comprises or encodes a TP53RK shRNA or siRNA comprising the sequence of: CAGTCCACTATGGAGACTGAA (SEQ ID NO:5); GGUAGAAGAAUGUGUAUGA (SEQ ID NO:6); GCUGAACAUUGUGCUCAUA (SEQ ID NO:8); or GUACCCAUCCCAACACUGA (SEQ ID NO:9),
or a reverse complement thereof.

2. The method of claim 1, further comprising administering to the subject thalidomide or an analog thereof.

3. The method of claim 1, further comprising administering to the subject melphalan.

4. The method of claim 1, further comprising administering to the subject prednisone.

5. The method of claim 1, further comprising administering to the subject doxorubicin or doxorubicin HCL liposome injection.

6. The method of claim 1, further comprising administering to the subject bortezomib.

* * * * *

SEQUENCE LISTING

```
<160> NUMBER OF SEQ ID NOS: 64

<210> SEQ ID NO 1
<211> LENGTH: 252
<212> TYPE: PRT
<213> ORGANISM: Homo sapiens

<400> SEQUENCE: 1

Arg Ala Ala Ala Arg Ala Thr Thr Pro Ala Asp Gly Glu Glu Pro Ala
1               5                   10                  15

Pro Glu Ala Glu Ala Leu Ala Ala Ala Arg Glu Arg Ser Ser Arg Phe
                20                  25                  30

Leu Ser Gly Leu Glu Leu Val Lys Gln Gly Ala Glu Ala Arg Val Phe
            35                  40                  45

Arg Gly Arg Phe Gln Gly Arg Ala Ala Val Ile Lys His Arg Phe Pro
        50                  55                  60

Lys Gly Tyr Arg His Pro Ala Leu Glu Ala Arg Leu Gly Arg Arg Arg
65                  70                  75                  80

Thr Val Gln Glu Ala Arg Ala Leu Leu Arg Cys Arg Arg Ala Gly Ile
                85                  90                  95

Ser Ala Pro Trp Phe Phe Val Asp Tyr Ala Ser Asn Cys Leu Tyr Met
                100                 105                 110

Glu Glu Ile Glu Gly Ser Val Thr Val Arg Asp Tyr Ile Gln Ser Thr
            115                 120                 125
```

```
Met Glu Thr Glu Lys Thr Pro Gln Gly Leu Ser Asn Leu Ala Lys Thr
    130                 135                 140

Ile Gly Gln Val Leu Ala Arg Met His Asp Glu Asp Leu Ile His Gly
145                 150                 155                 160

Asp Leu Thr Thr Ser Asn Met Leu Leu Lys Pro Pro Leu Glu Gln Leu
                165                 170                 175

Asn Ile Val Leu Ile Asp Phe Gly Leu Ser Phe Ile Ser Ala Leu Pro
                180                 185                 190

Glu Asp Lys Gly Val Asp Leu Tyr Val Leu Glu Lys Ala Phe Leu Ser
            195                 200                 205

Thr His Pro Asn Thr Glu Thr Val Phe Glu Ala Phe Leu Lys Ser Tyr
    210                 215                 220

Ser Thr Ser Ser Lys Lys Ala Arg Pro Val Leu Lys Lys Leu Asp Glu
225                 230                 235                 240

Val Arg Leu Arg Gly Arg Lys Arg Ser Met Val Gly
                245                 250

<210> SEQ ID NO 2
<211> LENGTH: 3384
<212> TYPE: DNA
<213> ORGANISM: Homo sapiens

<400> SEQUENCE: 2
ggggccacaa gagcccttcc tgcagggaac ctcaggcttc agagagccga aaagttggga      60
ggcgtaacca cttacaggcc ggaagtgtcc ggggtggacg cattcgggta gccgaagaag     120
tcccaggatt gccgaagaag tcccaggatt tccgaagcga gccgaagcat cgcgacagtt     180
ttcagagaca gctgatcggt tggagctgtt gcgccgagca gtcatggcgg cggccagagc     240
tactacgccg gccgatggcg aggagcccgc cccggaggct gaggctctgg ccgcagcccg     300
ggagcggagc agccgcttct tgagcggcct ggagctggtg aagcagggtg ccgaggcgcg     360
cgtgttccgt ggccgcttcc agggccgcgc ggcggtgatc aagcaccgct tccccaaggg     420
ctaccggcac ccggcgctgg aggcgcggct tggcagacgg cggacggtgc aggaggcccg     480
ggcgctcctc cgctgtcgcc gcgctggaat atctgcccca gttgtctttt ttgtggacta     540
tgcttccaac tgcttatata tggaagaaat tgaaggctca gtgactgttc gagattatat     600
tcagtccact atggagactg aaaaaactcc ccagggtctc tccaacttag ccaagacaat     660
tgggcaggtt ttggctcgaa tgcacgatga agacctcatt catggtgatc tcaccacctc     720
caacatgctc ctgaaacccc ccctggaaca gctgaacatt gtgctcatag actttgggct     780
gagtttcatt tcagcacttc cagaggataa gggagtagac ctctatgtcc tggagaaggc     840
cttcctcagt acccatccca cactgaaac tgtgtttgaa gcctttctga gagctactc      900 cacctcctcc aaaaaggcca ggccagtgct aaaaaaatta gatgaagtgc gcctgagagg     960
aagaaagagg tccatggttg gtagaagaa tgtgtatgac aaccacacac agtgaagctc    1020
ttttttcaaa gtaaatttga agaaatgcta caagtatgag atgagatcta agtaaaggtg    1080
ttaagatatt tttaagtggt atgtgatcgt gtcattatca tctgcacttc actcaagagc    1140
ttactatgtg tctaagtcat gttctaggca gaattgggta tttaaagtaa attgaggaca    1200
ggcttctccc agattgtgac atgtatatct cagatacatg ggtgtggcat tgaaccacat    1260
aatgagaaca ttattctctt tttagtcctt gtgagacaag gatgaagtct cagttgctga    1320
tactcgctga gcttactggc cctctaaccc agtgtttttt tttgttgttg ttgtgtacat    1380
```

-continued

```
gttatatttta ttttgaaacc agtttaatgg gatacaacca gcattttaaa aaatgaaata    1440
gaatacagca tggaaaatat cagtgtattg ttttatgaaa ctttcacgtg tatatataga    1500
ccaaggatat gtgctgagtt ttgatgtcaa atatatttct ctttcagggt catgatcaaa    1560
aaatgaaaag tctgcttaac tccaatttct cttttaaaaa agcagactta cagctttcag    1620
gcaactgaaa ttcatgttaa catgtttta tttttattgc tttgtatttt tgtggttacc     1680
ttctaagaca agtgattgat ctaaagttcc ttttaagttt ataccgctaa acaaactgag    1740
ttgatttcta tcacaggcag taagtaggta gagcaaaaat ggtgaagtga cttgtgaaga    1800
ctgaagtttg atgaagtctg gtttaaggca caggtaaact gagtgtggat gcaaaagtac    1860
caggagctag cttttaacct tgcccagcct cagtttcttt tcttagaaga agctatgttt    1920
gggtgggaag ggaagagagg gataagaaaa tacctttctt ccttgtaaac tccaatcaac    1980
aaacatattt tgagtgcctt tgtgttcct tggcaccctg ttgggtattg ggtacttggc     2040
accctgttgg gtattgggta caatggtgag ccagacagac acagcgcctg tccttttgta    2100
agaatattta tttttataaa aaagtataaa gtatacagtg ggatgttttg atatacatta    2160
tgaaatgatt gctacagctg agctaattaa cacccatcac ctcacatagt tactgtcttg    2220
tttcttaata tggacatttg cagctatgaa tttccctctg cacactgttg tcatcacaca    2280
ctctcagttt tggtattttg tgttttttgtt ttcattcatc tcaaagtatt ttctaatttc   2340
ccttgtgatt tcttctttga ccccttgatt gtttagaaat ctgttaattt ccacacattt    2400
gtaaatgttc caatttttct tttgttattg ccagcttcat tccattgtgt tcagagatga    2460
tacagtcagt gcctgttctt atgaagcaaa cattctataa tagtaggacc agtaccctgt    2520
ctgtttcatt caccacagtc agcatgcccc aagtgcccag catggggcgg atggccagga    2580
atgagtgaaa acttcccttc ctgggtagtt gtgactagta gagaggaaaa ataatataat    2640
tgcctgctta ctgcatgcca ggcattgggc tgggaatttt tatattggat ctaaaataac    2700
tcttaagtta ggcattatcc ccatttata gatggagaaa ctggccccaa aaggtgggaa    2760
cttgtccaag acgtcacagg tagcaagagg tacttttacc tggctccaaa tctgtgttct    2820
ttccactgac aaatgagata tgggatatgg tgcatctta cagtactata ataagtattg     2880
gcgtataaca ttattttcaa ggaactccaa gggccacagg agctgacagg ttttcaatt     2940 aatattccca acatgaatga gatgcctcat tcctcagttt cctcacgtgt actataaggc    3000
tagtacctgc tttgttgggg tatggttggc tcgtgtgcat taagtcaaca aatccctagt    3060
tgatagggtt tggctgtgtc cccatccaaa tctcatcttg aattgttccc gtaatcccca    3120
cgtgacatgg gagggaccca gtgggaggta atttaatcct cggggcggct acctccgtgc    3180
tgttctcgtg atagcgagtg agttctcacg agatctgatg gttttataag gggcttttcc    3240
ctcttgttcg gcacttcctg ctgccacgtg gagaagggtg tgtttgtttc cccatctgcc    3300
atgattataa gttttctgag gcatccccag ccatgctgaa ctgtgagtta ttaaactttt    3360
cctttataaa ttaaaaaaaa aaaa                                           3384
```

<210> SEQ ID NO 3
<211> LENGTH: 174
<212> TYPE: PRT
<213> ORGANISM: Homo sapiens

<400> SEQUENCE: 3

```
Met Gln Leu Thr His Gln Leu Asp Leu Phe Pro Glu Cys Arg Val Thr
1               5                   10                  15
```

Leu Leu Leu Phe Lys Asp Val Lys Asn Ala Gly Asp Leu Arg Arg Lys
            20                  25                  30

Ala Met Glu Gly Thr Ile Asp Gly Ser Leu Ile Asn Pro Thr Val Ile
        35                  40                  45

Val Asp Pro Phe Gln Ile Leu Val Ala Ala Asn Lys Ala Val His Leu
    50                  55                  60

Tyr Lys Leu Gly Lys Met Lys Thr Arg Thr Leu Ser Thr Glu Ile Ile
65                  70                  75                  80

Phe Asn Leu Ser Pro Asn Asn Ile Ser Glu Ala Leu Lys Lys Phe
                85                  90                  95

Gly Ile Ser Ala Asn Asp Thr Ser Ile Leu Ile Val Tyr Ile Glu Glu
            100                 105                 110

Gly Glu Lys Gln Ile Asn Gln Glu Tyr Leu Ile Ser Gln Val Glu Gly
        115                 120                 125

His Gln Val Ser Leu Asn Leu Pro Glu Ile Met Asn Ile Thr Glu Val
    130                 135                 140

Lys Lys Ile Tyr Lys Leu Ser Ser Gln Glu Glu Ser Ile Gly Thr Leu
145                 150                 155                 160

Leu Asp Ala Ile Ile Cys Arg Met Ser Thr Lys Asp Val Leu
                165                 170

<210> SEQ ID NO 4
<211> LENGTH: 752
<212> TYPE: DNA
<213> ORGANISM: Homo sapiens

<400> SEQUENCE: 4
gaagaagacg gggattggcc atcgcttccg aagttgtgaa gctttgtttc ggagcgggag      60
ctcttccgag acgcactggg ggccggatgt agaatcctgc ttatctgtga aatgcagtta     120
acacatcagc tggacctatt tcccgaatgc agggtaaccc ttctgttatt taaagatgta     180
aaaaatgcgg gagacttgag aagaaaggcc atggaaggca ccatcgatgg atcactgata     240
aatcctacag tgattgttga tccatttcag atacttgtgg cagcaaacaa agcagttcac     300
ctctacaaac tgggaaaaat gaagacaaga actctatcta ctgaaattat tttcaacctt     360
tccccaaata caatatttc agaggctttg aaaaaatttg gtatctcagc aaatgacact     420
tcaattctaa ttgtttacat tgaagaggga gaaaaacaaa taatcaaga atacctaata     480 tctcaagtag aaggtcatca ggtttctctg aaaaatcttc ctgaaataat gaatattaca     540
gaagtcaaaa agatatataa actctcttca caagaagaaa gtattgggac attattggat     600
gctatcattt gtagaatgtc aacaaaagat gttttatgaa atgtcagaaa tattaacaaa     660
aattctcagc attaaagaaa acattgattt tcctttcctg actataaaac taattgtgca     720
ttatagaaaa gtttaaatca cagaatggta tt                                   752

<210> SEQ ID NO 5
<211> LENGTH: 21
<212> TYPE: DNA
<213> ORGANISM: Homo sapiens

<400> SEQUENCE: 5
cagtccacta tggagactga a                                                21

<210> SEQ ID NO 6
<211> LENGTH: 19
<212> TYPE: DNA
<213> ORGANISM: Artificial Sequence

```
<220> FEATURE:
<223> OTHER INFORMATION: TP53RK siRNA J-003108-09

<400> SEQUENCE: 6
gguagaagaa uguguauga                                                    19

<210> SEQ ID NO 7
<211> LENGTH: 19
<212> TYPE: DNA
<213> ORGANISM: Artificial Sequence
<220> FEATURE:
<223> OTHER INFORMATION: TP53RK siRNA J-003108-10

<400> SEQUENCE: 7
gcuuccaacu gcuuauaua                                                    19

<210> SEQ ID NO 8
<211> LENGTH: 19
<212> TYPE: DNA
<213> ORGANISM: Artificial Sequence
<220> FEATURE:
<223> OTHER INFORMATION: TP53RK siRNA J-003108-11

<400> SEQUENCE: 8
gcugaacauu gugcucaua                                                    19

<210> SEQ ID NO 9
<211> LENGTH: 19
<212> TYPE: DNA
<213> ORGANISM: Artificial Sequence
<220> FEATURE:
<223> OTHER INFORMATION: TP53RK siRNA J-003108-12

<400> SEQUENCE: 9
guacccaucc caacacuga                                                    19

<210> SEQ ID NO 10
<211> LENGTH: 21
<212> TYPE: DNA
<213> ORGANISM: Homo sapiens

<400> SEQUENCE: 10
cccaagcaat ggatgatttg a                                                 21

<210> SEQ ID NO 11
<211> LENGTH: 21
<212> TYPE: DNA
<213> ORGANISM: Homo sapiens

<400> SEQUENCE: 11
ggcattctgg gagcttcatc t                                                 21

<210> SEQ ID NO 12
<211> LENGTH: 18
<212> TYPE: DNA
<213> ORGANISM: Homo sapiens

<400> SEQUENCE: 12
ggcccctacc tccctaca                                                     18

<210> SEQ ID NO 13
<211> LENGTH: 21
<212> TYPE: DNA
<213> ORGANISM: Homo sapiens
```

```
<400> SEQUENCE: 13
ggggtttgtg ttgatttgtc a                                              21

<210> SEQ ID NO 14
<211> LENGTH: 20
<212> TYPE: DNA
<213> ORGANISM: Homo sapiens

<400> SEQUENCE: 14
atgttttcct gtgccctgag                                                20

<210> SEQ ID NO 15
<211> LENGTH: 20
<212> TYPE: DNA
<213> ORGANISM: Homo sapiens

<400> SEQUENCE: 15
atctgtggtg agggatgagg                                                20

<210> SEQ ID NO 16
<211> LENGTH: 18
<212> TYPE: DNA
<213> ORGANISM: Homo sapiens

<400> SEQUENCE: 16
tttttcgggt agtggaaa                                                  18

<210> SEQ ID NO 17
<211> LENGTH: 21
<212> TYPE: DNA
<213> ORGANISM: Homo sapiens

<400> SEQUENCE: 17
gcagtagaaa tacggctgca c                                              21

<210> SEQ ID NO 18
<211> LENGTH: 21
<212> TYPE: DNA
<213> ORGANISM: Homo sapiens

<400> SEQUENCE: 18
tggctcgaat gcacgatgaa g                                              21

<210> SEQ ID NO 19
<211> LENGTH: 23
<212> TYPE: DNA
<213> ORGANISM: Homo sapiens

<400> SEQUENCE: 19
tgaaactcag cccaaagtct atg                                            23

<210> SEQ ID NO 20
<211> LENGTH: 21
<212> TYPE: DNA
<213> ORGANISM: Homo sapiens

<400> SEQUENCE: 20
ttccgtgatc cttttgagtg c                                              21

<210> SEQ ID NO 21
<211> LENGTH: 19
<212> TYPE: DNA
<213> ORGANISM: Homo sapiens
```

```
<400> SEQUENCE: 21
ctcgcgttat gtgcgacga                                                    19

<210> SEQ ID NO 22
<211> LENGTH: 21
<212> TYPE: DNA
<213> ORGANISM: Homo sapiens

<400> SEQUENCE: 22
gctcatacag acccgcatga t                                                 21

<210> SEQ ID NO 23
<211> LENGTH: 21
<212> TYPE: DNA
<213> ORGANISM: Homo sapiens

<400> SEQUENCE: 23
aactggaacc atctccgagg t                                                 21

<210> SEQ ID NO 24
<211> LENGTH: 20
<212> TYPE: DNA
<213> ORGANISM: Homo sapiens

<400> SEQUENCE: 24
gaaggtgaag gtcggagtca                                                   20

<210> SEQ ID NO 25
<211> LENGTH: 22
<212> TYPE: DNA
<213> ORGANISM: Homo sapiens

<400> SEQUENCE: 25
ggggtcattg atggcaacaa ta                                                22

<210> SEQ ID NO 26
<211> LENGTH: 22
<212> TYPE: DNA
<213> ORGANISM: Homo sapiens

<400> SEQUENCE: 26
acttcggctt taagacgcta ga                                                22

<210> SEQ ID NO 27
<211> LENGTH: 23
<212> TYPE: DNA
<213> ORGANISM: Homo sapiens

<400> SEQUENCE: 27
gcatgagtaa accacctctc aga                                               23

<210> SEQ ID NO 28
<211> LENGTH: 21
<212> TYPE: DNA
<213> ORGANISM: Homo sapiens

<400> SEQUENCE: 28
ggggacctag agcaacttac t                                                 21

<210> SEQ ID NO 29
<211> LENGTH: 19
<212> TYPE: DNA
```

<213> ORGANISM: Homo sapiens

<400> SEQUENCE: 29
cagcgcagtc cttccaaat                                            19

<210> SEQ ID NO 30
<211> LENGTH: 21
<212> TYPE: DNA
<213> ORGANISM: Homo sapiens

<400> SEQUENCE: 30
aggaacgcat ctctgtagca g                                         21

<210> SEQ ID NO 31
<211> LENGTH: 20
<212> TYPE: DNA
<213> ORGANISM: Homo sapiens

<400> SEQUENCE: 31
agggcctctc ttatcccagc                                           20

<210> SEQ ID NO 32
<211> LENGTH: 21
<212> TYPE: DNA
<213> ORGANISM: Homo sapiens

<400> SEQUENCE: 32
tttctccgcc catacacagt g                                         21

<210> SEQ ID NO 33
<211> LENGTH: 21
<212> TYPE: DNA
<213> ORGANISM: Homo sapiens

<400> SEQUENCE: 33
agcacctcaa tctccagagg a                                         21

<210> SEQ ID NO 34
<211> LENGTH: 20
<212> TYPE: DNA
<213> ORGANISM: Homo sapiens

<400> SEQUENCE: 34
gctcaatcgg cactgggtat                                           20

<210> SEQ ID NO 35
<211> LENGTH: 21
<212> TYPE: DNA
<213> ORGANISM: Homo sapiens

<400> SEQUENCE: 35
acctgctact gccattccaa c                                         21

<210> SEQ ID NO 36
<211> LENGTH: 21
<212> TYPE: DNA
<213> ORGANISM: Artificial Sequence
<220> FEATURE:
<223> OTHER INFORMATION: shTP53RK #1 TRCN0000037522

<400> SEQUENCE: 36
cagtccacta tggagactga a                                         21

```
<210> SEQ ID NO 37
<211> LENGTH: 21
<212> TYPE: DNA
<213> ORGANISM: Artificial Sequence
<220> FEATURE:
<223> OTHER INFORMATION: shTP53RK #2 TRCN0000196805

<400> SEQUENCE: 37
gaagacctca ttcatggtga t                                              21

<210> SEQ ID NO 38
<211> LENGTH: 21
<212> TYPE: DNA
<213> ORGANISM: Artificial Sequence
<220> FEATURE:
<223> OTHER INFORMATION: shMYC TRCN0000039642

<400> SEQUENCE: 38
cctgagacag atcagcaaca a                                              21

<210> SEQ ID NO 39
<211> LENGTH: 21
<212> TYPE: DNA
<213> ORGANISM: Artificial Sequence
<220> FEATURE:
<223> OTHER INFORMATION: shp53 (A12) TRCN0000003753

<400> SEQUENCE: 39
cggcgcacag aggaagagaa t                                              21

<210> SEQ ID NO 40
<211> LENGTH: 21
<212> TYPE: DNA
<213> ORGANISM: Artificial Sequence
<220> FEATURE:
<223> OTHER INFORMATION: shP53 (B10) TRCN0000003756

<400> SEQUENCE: 40
caccatccac tacaactaca t                                              21

<210> SEQ ID NO 41
<211> LENGTH: 21
<212> TYPE: DNA
<213> ORGANISM: Artificial Sequence
<220> FEATURE:
<223> OTHER INFORMATION: shp53 (D1) TRCN0000003755

<400> SEQUENCE: 41
gtccagatga agctcccaga a                                              21

<210> SEQ ID NO 42
<211> LENGTH: 21
<212> TYPE: DNA
<213> ORGANISM: Artificial Sequence
<220> FEATURE:
<223> OTHER INFORMATION: shp53 (D6) TRCP0001527933

<400> SEQUENCE: 42
gagggatgtt tgggagatgt a                                              21

<210> SEQ ID NO 43
<211> LENGTH: 21
<212> TYPE: DNA
<213> ORGANISM: Artificial Sequence
<220> FEATURE:
<223> OTHER INFORMATION: shp53 (D9) TRCP0001527933
```

```
<400> SEQUENCE: 43
tcagacctat ggaaactact t                                              21

<210> SEQ ID NO 44
<211> LENGTH: 21
<212> TYPE: DNA
<213> ORGANISM: Artificial Sequence
<220> FEATURE:
<223> OTHER INFORMATION: shLuc (control) TRCN0000072246

<400> SEQUENCE: 44
caaatcacag aatcgtcgta t                                              21

<210> SEQ ID NO 45
<211> LENGTH: 19
<212> TYPE: DNA
<213> ORGANISM: Artificial Sequence
<220> FEATURE:
<223> OTHER INFORMATION: TP53RK siRNA J-003108-09

<400> SEQUENCE: 45
gguagaagaa uguguauga                                                 19

<210> SEQ ID NO 46
<211> LENGTH: 19
<212> TYPE: DNA
<213> ORGANISM: Artificial Sequence
<220> FEATURE:
<223> OTHER INFORMATION: TP53RK siRNA J-003108-10

<400> SEQUENCE: 46 gcuccaacu gcuuauaua                                                  19

<210> SEQ ID NO 47
<211> LENGTH: 19
<212> TYPE: DNA
<213> ORGANISM: Artificial Sequence
<220> FEATURE:
<223> OTHER INFORMATION: TP53RK siRNA J-003108-11

<400> SEQUENCE: 47
gcugaacauu gugcucaua                                                 19

<210> SEQ ID NO 48
<211> LENGTH: 19
<212> TYPE: DNA
<213> ORGANISM: Artificial Sequence
<220> FEATURE:
<223> OTHER INFORMATION: TP53RK siRNA J-003108-12

<400> SEQUENCE: 48
guacccaucc caacacuga                                                 19

<210> SEQ ID NO 49
<211> LENGTH: 19
<212> TYPE: DNA
<213> ORGANISM: Artificial Sequence
<220> FEATURE:
<223> OTHER INFORMATION: TP53 siRNA J-003329-14

<400> SEQUENCE: 49
gaaauuugcg uguggagua                                                 19

<210> SEQ ID NO 50
<211> LENGTH: 19
```

```
<212> TYPE: DNA
<213> ORGANISM: Artificial Sequence
<220> FEATURE:
<223> OTHER INFORMATION: TP53 siRNA J-003329-15

<400> SEQUENCE: 50
gugcagcugu ggguugauu                                                    19

<210> SEQ ID NO 51
<211> LENGTH: 19
<212> TYPE: DNA
<213> ORGANISM: Artificial Sequence
<220> FEATURE:
<223> OTHER INFORMATION: TP53 siRNA J-003329-16

<400> SEQUENCE: 51
gcagucagau ccuagcguc                                                    19

<210> SEQ ID NO 52
<211> LENGTH: 19
<212> TYPE: DNA
<213> ORGANISM: Artificial Sequence
<220> FEATURE:
<223> OTHER INFORMATION: TP53 siRNA J-003329-17

<400> SEQUENCE: 52
ggagaauauu ucacccuuc                                                    19

<210> SEQ ID NO 53
<211> LENGTH: 19
<212> TYPE: DNA
<213> ORGANISM: Artificial Sequence
<220> FEATURE:
<223> OTHER INFORMATION: MYC siRNA J-003282-26

<400> SEQUENCE: 53
cgauguuguu ucuguggaa                                                    19

<210> SEQ ID NO 54
<211> LENGTH: 19
<212> TYPE: DNA
<213> ORGANISM: Artificial Sequence
<220> FEATURE:
<223> OTHER INFORMATION: MYC siRNA J-003282-25

<400> SEQUENCE: 54
aacguuagcu ucaccaaca                                                    19

<210> SEQ ID NO 55
<211> LENGTH: 19
<212> TYPE: DNA
<213> ORGANISM: Artificial Sequence
<220> FEATURE:
<223> OTHER INFORMATION: MYC siRNA J-003282-24

<400> SEQUENCE: 55
gaacacacaa cgucuugga                                                    19

<210> SEQ ID NO 56
<211> LENGTH: 19
<212> TYPE: DNA
<213> ORGANISM: Artificial Sequence
<220> FEATURE:
<223> OTHER INFORMATION: MYC siRNA J-003282-23

<400> SEQUENCE: 56
```
acggaacucu ugugcguaa                                               19

<210> SEQ ID NO 57
<211> LENGTH: 19
<212> TYPE: DNA
<213> ORGANISM: Artificial Sequence
<220> FEATURE:
<223> OTHER INFORMATION: CRBN siRNA J-021086-12

<400> SEQUENCE: 57
cgacuucgcu gugaauuag                                               19

<210> SEQ ID NO 58
<211> LENGTH: 19
<212> TYPE: DNA
<213> ORGANISM: Artificial Sequence
<220> FEATURE:
<223> OTHER INFORMATION: CRBN siRNA J-021086-11

<400> SEQUENCE: 58
gacauuaccu cuucagcuu                                               19

<210> SEQ ID NO 59
<211> LENGTH: 19
<212> TYPE: DNA
<213> ORGANISM: Artificial Sequence
<220> FEATURE:
<223> OTHER INFORMATION: CRBN siRNA J-021086-10

<400> SEQUENCE: 59
guauaaggcu ugcaacuug                                               19

<210> SEQ ID NO 60
<211> LENGTH: 19
<212> TYPE: DNA
<213> ORGANISM: Artificial Sequence
<220> FEATURE:
<223> OTHER INFORMATION: CRBN siRNA J-021086-9

<400> SEQUENCE: 60
caauuagaau cccucaaua                                               19

<210> SEQ ID NO 61
<211> LENGTH: 19
<212> TYPE: DNA
<213> ORGANISM: Artificial Sequence
<220> FEATURE:
<223> OTHER INFORMATION: RRMI siRNA J-004270-05

<400> SEQUENCE: 61
uaugagggcu cuccaguua                                               19

<210> SEQ ID NO 62
<211> LENGTH: 19
<212> TYPE: DNA
<213> ORGANISM: Artificial Sequence
<220> FEATURE:
<223> OTHER INFORMATION: RRMI siRNA J-004270-06

<400> SEQUENCE: 62
ugagagaggu gcuuucauu                                               19

<210> SEQ ID NO 63
<211> LENGTH: 19
<212> TYPE: DNA
<213> ORGANISM: Artificial Sequence

```
<220> FEATURE:
<223> OTHER INFORMATION: RRMI siRNA J-004270-07

<400> SEQUENCE: 63
uggaagaccu cuauaacua                                                 19

<210> SEQ ID NO 64
<211> LENGTH: 19
<212> TYPE: DNA
<213> ORGANISM: Artificial Sequence
<220> FEATURE:
<223> OTHER INFORMATION: RRMI siRNA J-004270-08

<400> SEQUENCE: 64
cuacuaagca cccugacua                                                 19
```